(12) United States Patent
Burrell et al.

(10) Patent No.: US 7,852,470 B2
(45) Date of Patent: Dec. 14, 2010

(54) SYSTEM AND METHOD FOR IMPROVED BIODETECTION

(75) Inventors: Michael Craig Burrell, Clifton Park, NY (US); Frank Mondello, Niskayuna, NY (US); Tracy Lynn Paxon, Waterford, NY (US); William Scott Sutherland, Murrieta, CA (US); Christopher Montalbano, Huntington, NY (US); Gregory Montalbano, Huntington, NY (US); Aaron Klein, Brightwaters, NY (US)

(73) Assignee: Morpho Detection, Inc., Newark, CA (US)

( * ) Notice: Subject to any disclaimer, the term of this patent is extended or adjusted under 35 U.S.C. 154(b) by 403 days.

(21) Appl. No.: 11/966,332

(22) Filed: Dec. 28, 2007

(65) Prior Publication Data

US 2009/0168052 A1     Jul. 2, 2009

(51) Int. Cl.
*G01J 3/44* (2006.01)
(52) U.S. Cl. ...................................... 356/301
(58) Field of Classification Search ................. 356/301, 356/72–73
See application file for complete search history.

(56) References Cited

U.S. PATENT DOCUMENTS

| | | | |
|---|---|---|---|
| 6,033,574 A | 3/2000 | Siddiqi | |
| 6,228,268 B1 | 5/2001 | Siddiqi | |
| 6,231,760 B1 | 5/2001 | Siddiqi | |
| 6,500,343 B2 | 12/2002 | Siddiqi | |
| 6,514,767 B1 | 2/2003 | Natan | |
| 6,747,735 B2 | 6/2004 | Chen et al. | |
| 6,884,357 B2 | 4/2005 | Siddiqi | |
| 2004/0234958 A1 | 11/2004 | Smith et al. | |
| 2006/0023209 A1 | 2/2006 | Lee | |
| 2006/0054506 A1 | 3/2006 | Natan | |
| 2006/0055919 A1 | 3/2006 | Lee | |
| 2007/0015288 A1 | 1/2007 | Holteen et al. | |
| 2007/0058165 A1 | 3/2007 | Mondello | |
| 2007/0059203 A1 | 3/2007 | Burrell | |
| 2007/0292941 A1* | 12/2007 | Handique et al. | ........ 435/288.7 |

FOREIGN PATENT DOCUMENTS

| | | |
|---|---|---|
| EP | 00810905 B1 | 11/1998 |
| EP | 01248680 B1 | 10/2005 |

\* cited by examiner

*Primary Examiner*—Tarifur Chowdhury
*Assistant Examiner*—Abdullahi Nur
(74) *Attorney, Agent, or Firm*—Armstrong Teasdale LLP

(57) ABSTRACT

A portable substance identification system and method are configured to identify at least one detection target faster and with greater accuracy than is possible using prior substance identification systems and/or prior substance identification techniques. An embodiment of the portable substance identification system includes a portable substance identification device containing a Raman spectrometer, and a collection stem that includes a dry collector. One or more reservoirs for a liquid medium and/or a reagent can be formed in a cartridge that is configured to couple with a portable substance identification device. The cartridge has a chamber in which the reagent, liquid medium, and a detection target picked up by the dry collector are mixed. A magnet, positioned at a slant angle, can be used to form at least one pellet of aggregated magnetic particles within a pellet forming area of the chamber. The pellet is formed to maximize its surface area.

13 Claims, 16 Drawing Sheets

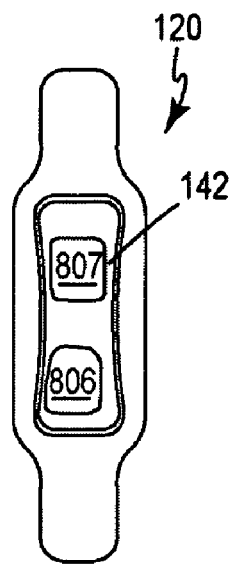 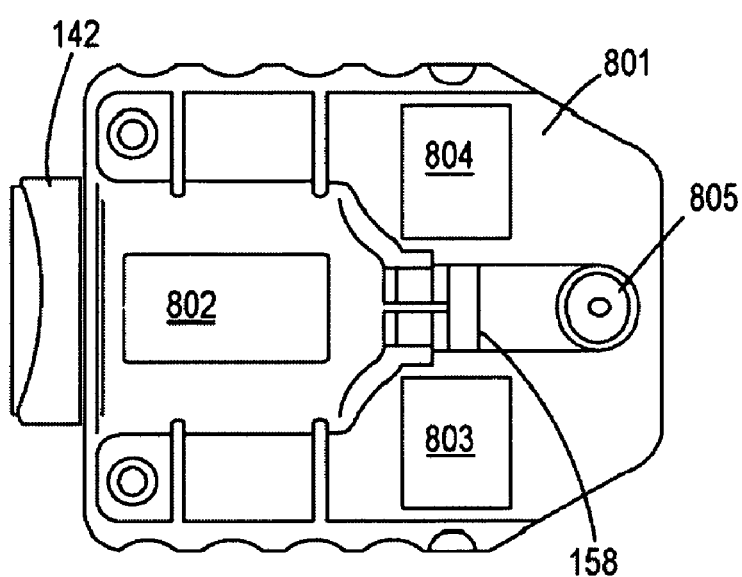
FIG. 9  FIG. 10
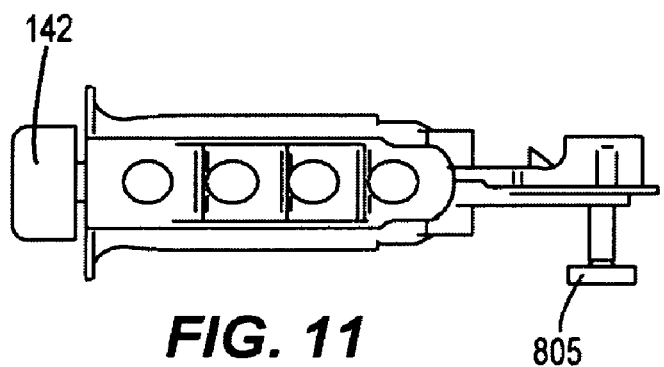
FIG. 11

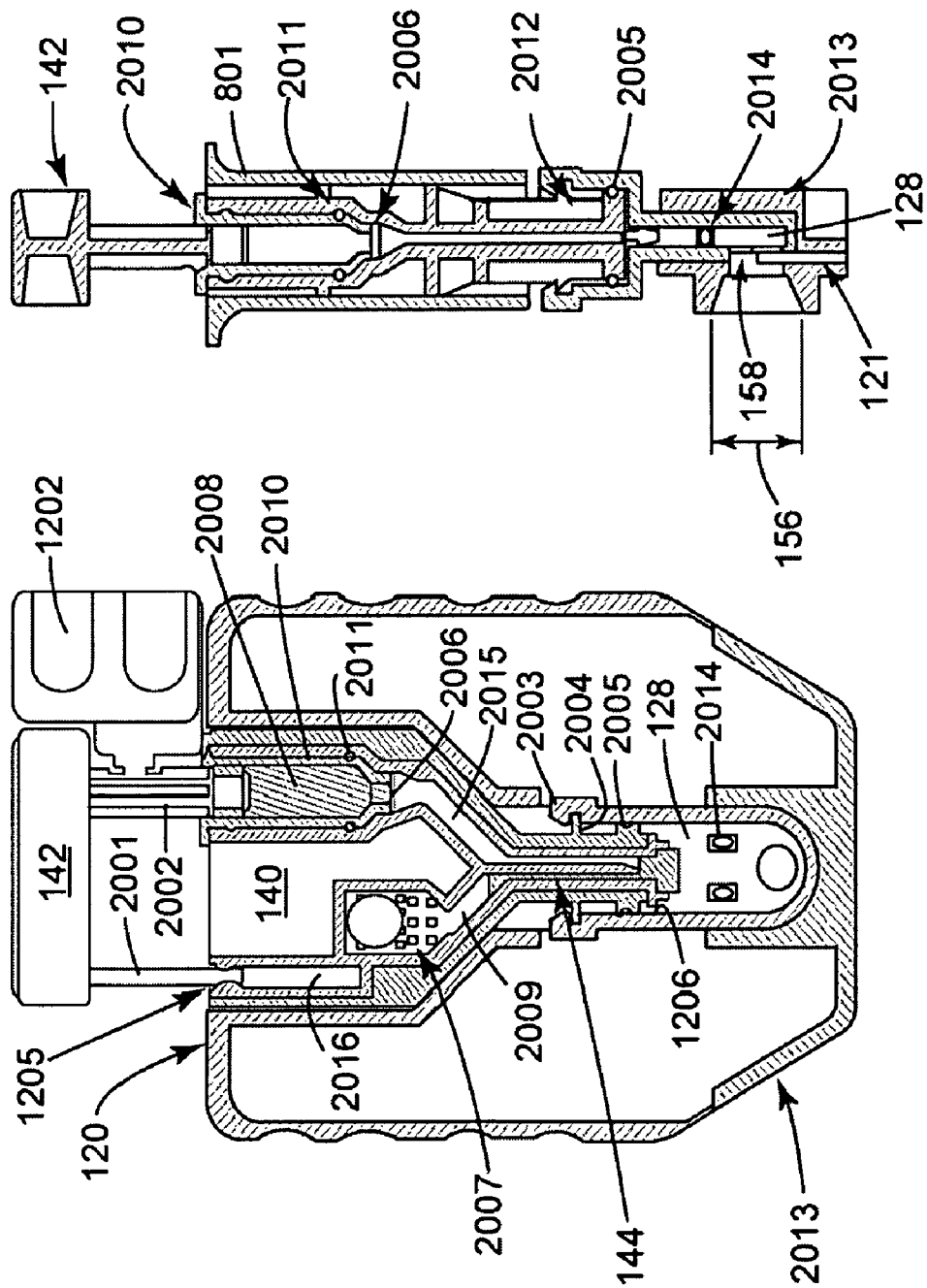

SYSTEM AND METHOD FOR IMPROVED BIODETECTION

BACKGROUND

1. Field of the Invention

The field of the invention relates to detection systems generally, and more particularly, to a portable substance identification system and method of using the same that are configured to analyze and identify at least one detection target tagged to at least one magnetic particle, which are magnetically clustered within a liquid medium on a wall of a chamber.

2. Discussion of Related Art

Personnel working in law enforcement, customs and border operations, forensics labs, military facilities, and in emergency first responder roles often need to analyze samples of unknown substances (such as pills, powders, pastes, liquids, and so forth) in the field to determine whether they comprise pathogens, explosives, pharmaceuticals, and so forth. Portable substance identification systems have been developed that deliver fast, accurate, low-cost identification of such unknown substances in the field. Such systems can objectively and non-destructively analyze and identify a broad range of detection targets in seconds. To prevent contamination and/or loss of evidence, some portable substance identification systems have the ability to analyze small quantities of detection targets (solids) that are either within their original packaging or that are placed within small containers, such as cylindrical vials formed of clear glass or plastic.

One subset of substance identification systems, employ Raman-based spectroscopic techniques to identify detection targets (defined below). Spectroscopy is a branch of physics that studies the molecular or atomic structure of a detection target by measuring and interpreting the interaction between different wavelengths of electromagnetic radiation absorbed or emitted by the detection target when it is impinged by electromagnetic radiation. In particular, Raman spectroscopy analyzes the frequency shifts from monochromatic light, usually from a laser in the visible, near-infrared, or ultraviolet range, that in elastically scatters off molecules of the detection target. Because it is very specific for the chemical bonds in molecules, the frequency shift information obtained from Raman spectroscopy provides a fingerprint by which the molecules can be uniquely identified.

The main challenge of Raman spectroscopy is separating the weak in elastically scattered laser light from the more intense elastically scattered laser light. Accordingly, several types of Raman spectroscopy have been developed. One variation, called Surface-Enhanced Raman Spectroscopy ("SERS"), involves chemisorption or physisorption of molecules of a detection target to a substrate made of or containing a metal such as silver or gold. The incident and scattered light is greatly amplified due to interactions of the light with the detection target and the metal surface.

SERS may also be used to analyze molecules of a detection target that are attached to the surface of a single metallic particle, such as a nanoparticle. A SERS-active particle contains a Raman enhancing metal and has a surface to which a Raman-active molecule(s) is (are) associated or bound. Such SERS-active particles can be used as optically responsive tags in immunoassays when bound to a receptor (antibody) that uniquely attracts a target molecule of interest. Some SERS particles (and/or SERS-active particles) are permanently magnetized, are paramagnetic or are super-paramagnetic. Materials that are either paramagnetic or super-paramagnetic become magnetized only when subjected to a magnetic field. For simplicity, the term "magnetic" will be employed hereinafter and understood to include permanently magnetized, magnetically permeable, paramagnetic, and super-paramagnetic materials and/or particles. Similarly, the term "particles" will be employed and understood to include both non-nanosized particles and nanoparticles.

The magnetizable (SERS or SERS-active) particles discussed above have been used to magnetically mix and isolate at least one detection target from a non-magnetic liquid test medium. The magnetic mixing process typically involves adding paramagnetic or super-paramagnetic particles to a liquid medium and agitating the liquid medium to bind the detection targets(s) to the particles by affinity reaction. Agitating the liquid medium is accomplished by shaking, swirling, rocking, rotating, or similarly manipulating the partially-filled container holding the liquid medium. Additionally, agitation has been accomplished by creating a magnetic field gradient in the liquid medium to induce the magnetically responsive particles to move towards the inside wall of the container, and then achieving relative movement between the magnetic source and the aggregating magnetically responsive particles to mix the magnetically responsive particles with the liquid medium and to ensure optimum binding of the detection target(s) by affinity reaction.

The isolation process has been performed by positioning a fixed magnetic source near an exterior portion of the container to immobilize the paramagnetic particles as a relatively compact aggregate on the inside wall of the container nearest to the magnetic source. A laser beam, from a laser source positioned on a side of the container opposite the magnet, is then shined through the container and onto the aggregate of paramagnetic particles, and the light scattered from the aggregate of paramagnetic particles is spectroscopically analyzed, using known techniques, to identify one or more detection targets.

The laser beam can be shined through the liquid medium, or the liquid medium can be evacuated from the container before the laser is activated. Shining the laser beam through the liquid medium, however, has several disadvantages. First, background signal(s) may be emitted from the liquid medium and/or from interfering species contained in the liquid medium. If so, the intensity of light scattered from the aggregate of paramagnetic particles must be greater than the intensity of the background signal(s) to be considered a positive indicator of the detection target(s). If the liquid medium is turbid, the laser beam may be attenuated before reaching the aggregate of paramagnetic particles or the intensity of the laser light scattered from the aggregate of paramagnetic particles may be attenuated on its way back to the detector.

A disadvantage of the known apparatus and methods that are configured to perform magnetic mixing/separation is that they are not optimized for use in portable substance detection systems that employ laser-based Raman spectroscopy. Another disadvantage is that these known apparatus and methods are not configured to form a pellet of magnetic particles such that the pellet is configured to maximize a ratio of the pellet's surface area to the pellet's volume. Yet another disadvantage is that the known apparatus and methods also are not configured to form multiple pellets that can each be interrogated by a laser beam to increase accuracy of identification.

For at least these reasons, there is a need for a portable substance identification system that is uniquely configured to: immerse at least one detection target in a liquid medium; combine the immersed detection targets and the liquid medium with magnetic, optically responsive, and/or perishable reagents; mix the detection targets, liquid medium, and the one or more magnetic, optically responsive, and/or perishable reagents; aggregate a pellet that has a maximized ratio of surface area to volume; and analyze the tagged detection target(s), if any, using laser-based Raman spectroscopy.

SUMMARY

Described herein are systems, devices, and methods that overcome at least the exemplary deficiencies and/or disadvantages of the prior art highlighted above. Embodiments of the systems, devices, and methods improve Raman-based detection and identification of at least one detection target (defined above).

Illustratively, a portable substance identification system may be configured to identify at least one detection target faster and with greater accuracy than is possible using prior substance identification systems and/or prior substance identification techniques. As will be explained in greater detail below, an embodiment of the portable substance identification system may include: a portable substance identification device containing a Raman spectrometer, and a collection stem that includes a dry collector. The cartridge may include a chamber that is configured to contain a liquid medium and/or at least one reagent (non-limiting examples of which include optically responsive tags, magnetic particles, and antibodies).

The portable substance identification system may also include a cartridge having a reaction chamber in which the reagents, liquid medium, and at least one detection target picked up by a dry or wetted collector are mixed. The portable substance identification system may also include at least one magnet configured to form at least one pellet of aggregated magnetic particles within a pellet forming area of the chamber. The pellet may be formed in a way that maximizes a surface area of the pellet for scanning by Raman spectrometer.

Illustratively, a method may include wetting a collector of a collection stem; collecting a sample on the wetted collector; and inserting the collector into a chamber. The chamber, which may be located in a cartridge configured to removably couple with a portable substance identification device or which may be located in the portable substance identification device itself, may be a reaction chamber or a chamber coupled with a reaction chamber.

Illustratively, a substance detection system may include a cartridge and a chamber formed in the cartridge. The chamber may include a pellet forming area having a predetermined geometry that is configured to maximize a ratio of a pellet surface area to a pellet volume. A reservoir may be formed in the cartridge and configured to contain at least one of a liquid medium and one or more reagents. In addition, the reservoir is selectably coupled with the chamber. Additionally, a magnet is coupled with the cartridge and moveable to the pellet forming area. The substance detection system may further include a collection stem having a dry collector. The dry collector is engageable with the chamber of the cartridge, and is configured to collect a sample.

Illustratively, a method may include collecting a sample on a dry collector of a collection stem; inserting the collected sample and dry collection stem into a chamber; mixing the collected sample with the liquid medium and one or more reagents; and forming a pellet of the one or more magnetic particles, the pellet having a maximized surface area.

Illustratively, a method may include mixing the collected sample in a reaction chamber with a liquid medium and at least one reagent; configuring the pellet to maximize a surface area of the pellet; and analyzing the pellet with a Raman spectrometer.

Advantages, or technical effects, associated with embodiments of the invention include, but are not limited to: faster binding reaction between reagents and detection targets; decreased non-specific binding between magnetic particles and optically responsive tags; increased pellet surface area for interrogation by a laser beam; increased detection sensitivity and reduced false positives from dithered laser scanning of aggregated magnetic particles; analysis and identification of at least one detection target using a single collection sample; and long shelf life with use of freeze-dried reagents, e.g., perishable reagents, and/or with separate storage of reagents and a liquid medium in a single device.

The embodiments of the invention described herein are also advantageous, in part, because they eliminate most or all of the problems associated with shining the laser beam from a side of the chamber that is opposite a pellet, as previously taught. Some problems that are eliminated by embodiments of the apparatus and methods include, but are not limited to: undesired interaction of the laser beam with the liquid medium, undesired fluorescence background caused by interfering species, and attenuation of the laser beam and/or the light scattered from the pellet. Because embodiments of the invention configure the laser beam to interrogate the pellet from the same side of the chamber as the magnet, background signals that might result from laser beam passing through the liquid medium itself and/or undesired fluorescence background signals that might result from laser light scattered from unbound Raman tags in the liquid medium are reduced or eliminated. This means that, in embodiments of the invention, the intensity of light scattered from the pellet can be less than the intensity that would have been formerly required to be a positive indicator of the detection target(s). Additionally, embodiments of the invention can identify the detection target(s) even when the liquid medium is turbid because, in embodiments of the invention, both the laser beam that reaches the pellet and the light scattered from the pellet are not attenuated by the liquid medium.

Such exemplary and non-limiting advantages, as well as others that will be appreciated by readers of this disclosure, can increase the overall sensitivity of portable substance identification systems while rendering them more user-friendly and easier to use than prior systems and methods.

Other features and advantages of the disclosure will become apparent by reference to the following description taken in connection with the accompanying drawings.

BRIEF DESCRIPTION OF THE DRAWINGS

For a more complete understanding of the apparatus and methods described herein, and the advantages thereof, reference is now made to the following descriptions taken in conjunction with the accompanying drawings, in which:

FIG. 9 is a top view of the cartridge of FIG. 8;

FIG. 10 is a front view of the cartridge of FIG. 8;

FIG. 11 is a side view of the cartridge of FIG. 8;

FIG. 20 is a front sectional view of an embodiment of the cartridge of FIGS. 1, 8, 9, 10, 11, 12, 13, 15, 16, and 18 and an embodiment of the collection stem of FIG. 13;

FIG. 21 is a side sectional view of an embodiment of the cartridge and the collection stem of FIG. 20;

Like reference characters designate identical or corresponding components and units throughout the several views. Unless otherwise expressly noted, the dotted/dashed lines in the figures represent optional components that may be included in various embodiments of the invention.

DETAILED DESCRIPTION

As used herein, the term "detection target" refers to any substance (e.g., chemical elements and their compounds), microorganism, or molecule of interest that a substance identification system, equipped with any type of Raman spectrometer, may be configured to analyze and identify. The terms "Raman spectrometer" and "spectrometer" broadly refer to any type of fluorescence, phosphorescence, calorimetric, Surface-Enhanced Raman Spectroscopy ("SERS") and other tags, as well as the instruments required to read the tags. Examples of instruments required to read the tags include, but are not limited to, a laser source, a laser detector, a laser controller, any necessary optics, circuitry, computer software, computer hardware, computer firmware, power source, magnet, and the like required to generate a laser-stimulated emission from a detection target bound to a magnetic particle or to a tag.

A "detection target" may include, but is not limited to, a pathogen, a toxin, a simulant, an explosive, a pharmaceutical, a narcotic, and the like. The term "simulant" refers to a harmless substance or microorganism that mimics at least one physical, chemical, or physiological characteristic of a hazardous (or potentially hazardous) substance or microorganism. For example, since a pathogen such as *Bacillus anthracis* is too toxic for experimentation, a non-toxic organism such as *Bacillus subtilis* (having same size, shape, species, etc.) may be used instead.

In this document, the term "reagent" refers to any substance or group of substances having biospecific binding affinity for a given detection target to the substantial exclusion of other substances. The term "reagent" includes magnetic particles, optically responsive tags, and perishable reagents. Non-limiting examples of perishable reagents include antibodies, aptamers, lectins, nucleic acids, enzymes, fragments of antibodies, etc. The term "detection target" may also refer to substances that are capable of being biospecifically tagged by (e.g., recognized by and bound to) a reagent. In addition to the examples of detection targets given above, other non-limiting examples of detection targets may include haptens, antigens, predetermined chemicals (such as pharmaceuticals, explosives, etc.), cell structures having at least one characteristic determinant, and the like.

As used herein, an element or step recited in the singular and proceeded with the word "a" or "an" should be understood as not excluding plural said elements or steps, unless such exclusion is explicitly recited. Furthermore, references to "one embodiment" of the present invention should not be interpreted as excluding the existence of additional embodiments that also incorporate the recited features.

Figure 1:
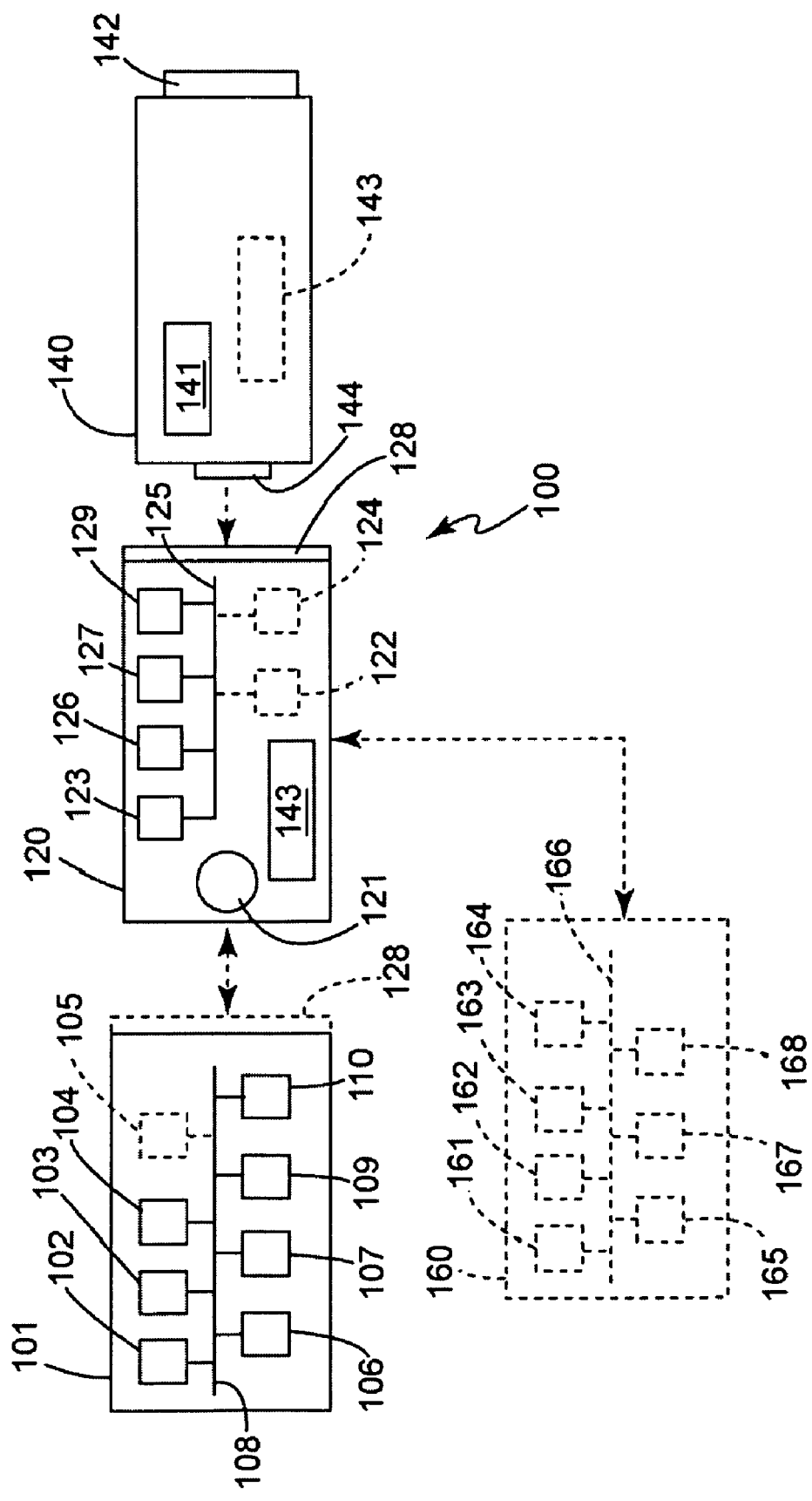
FIG. 1 is a diagram illustrating an embodiment of a portable substance identification system.

FIG. 1 is a diagram of an embodiment of a portable substance identification system 100 that schematically illustrates how various components of the system 100 may be configured and how each of the various components of the system 100 may interrelate to each other.

An embodiment of a portable substance identification system 100 may include at least a portable substance identification device 101, a cartridge 120, and a collection stem 140. Another embodiment of the portable substance identification system 100 may optionally include an agitator 160. Each of these components of the portable substance identification system 100 will now be described in turn, first with reference to their interaction with each other, and second with reference to their sub-components and methods of operation.

The portable substance identification device 101 contains all the sub-components necessary to analyze suspicious substances in the field for the presence of at least one detection target. In particular, the sub-components of the portable substance identification device 101 may be configured to perform laser-based Raman spectroscopy of a pellet formed of aggregated magnetic particles and to indicate the results visually and/or audibly. The magnetic particles may be coated with one or more optically responsive tags.

The disposable, or reusable, cartridge 120 may function to mix a collected sample in a liquid medium that includes at least one reagent. The cartridge 120 may also function to form a pellet of aggregated magnetic particles in a manner that maximizes the pellet's ratio of surface area to volume. The cartridge 120 may further function to position the pellet proximate a portion of the portable substance identification device so the pellet can be scanned by a laser beam.

The collection stem 140, which may be disposable, may function to collect a collected sample of a suspicious substance in a safe manner that prevents contamination, or further contamination, of a user of the portable substance identification system 100. The collection stem 140 may further function to transmit at least the collected sample safely into a chamber 128 for admixing in the liquid medium with the at least one reagent. In an embodiment, a "sandwich" may be formed that includes a SERS optically responsive tag that is coupled with a detection target that is coupled with a magnetic particle.

Portable Substance Identification Device

Still referring to FIG. 1 and turning now to the description of the sub-components of the portable substance identification system 100, the portable substance identification device 101 may include a user interface 102, a computer processor 103, a computer readable memory 104, an optional communicator 105, a display 110, a power source 107, a laser source 109, and a Raman spectrometer 106—each of a type known in the art. Each of these subcomponents may be coupled with the others via electrical/digital circuitry such as bus 108. The Raman spectrometer 106 may include a laser source and associated computer hardware/software, electrical circuitry, and the like that are configured to provide laser-based Raman spectroscopy of at least one pellet of aggregated magnetic particles. The communicator 105 can be a radio-frequency identification tag reader or a wireless transceiver.

The portable substance identification device 101 may optionally include the chamber 128; but preferably, the chamber 128 is formed in the cartridge 120. As shown in the following Figures and as further described below, the chamber 128 can be a compartment or an enclosed space configured to contain a liquid medium. The chamber 128 may be configured to receive and/or retain a portion of the collection stem 140. One or more of the subcomponents of the portable substance identification device 101 may be enclosed in a housing (not shown).

The laser-based Raman spectroscopy performed by an embodiment of the portable substance identification device 101 may include shining a laser beam onto the pellet from the laser source 109, positioned on the same side of the chamber 128 as a magnet 121, which may be included in the cartridge 120. In an alternate embodiment, the magnet 121 could be included in the portable substance identification device 101 instead of the cartridge 120.

Cartridge

Referring still to FIG. 1, the cartridge 120 may have any suitable shape. The material used to form the cartridge housing and/or subcomponents of the cartridge 120 may be, but is not limited to, plastic, polymers, metal, metal alloys, and combinations thereof.

The cartridge 120 may include a chamber 128 and a magnet 121. In another embodiment, the cartridge 120 may optionally include a power source 124, a user interface 123, a computer processor 126, a computer-readable memory 127, a display 129, and/or an RFID card or tag, each of the type known in the art. The cartridge 120 may be configured to store at least one of: one or more reagents 143 and a liquid medium 141. In one embodiment, the at least one reagent 143 is stored separately from a liquid medium 141. The reagent 143 may be a freeze-dried reagent having a predetermined shelf life. The reagent 143 may also be at least one of one or more magnetic particles and one or more optically responsive tags.

The chamber 128 of the cartridge 120 may be configured to safely contain, without leakage or spillage, a liquid medium 141, such as a buffer solution, that is passed from a reservoir 2010 (FIG. 20) to the chamber 128 when a user depresses an actuator 142 (See also, FIG. 20).

The magnet 121 may be permanently magnetic or electromagnetic. The magnet may be shaped to arrange a magnetic field gradient to maximize a surface area of the pellet. Additionally or alternatively, the magnet 121 may be shaped to permit a laser beam emitted by a laser source 109 (FIG. 1), which may form part of the Raman spectrometer 106, to scan as much of the pellet as possible. If electromagnetic, the magnet 121 may be electrically coupled with the power source 124. Alternatively, if electromagnetic, the magnet 121 may be electrically coupled with the power source 107 of the portable substance identification device 101.

Additionally, the magnet 121 may be a single magnet or multiple magnets. The magnet 121 may be manually or automatically movable towards, away from, and/or along a wall of the chamber 128. The magnet 121 may be used to form a pellet of magnetic particles on a wall of the chamber 128. Additionally or alternatively, the magnet 121 may be used to magnetically mix at least one detection target and at least one reagent that are suspended within a liquid medium in the chamber 128. Optionally, the magnet 121 may be shielded, using known shielding techniques and materials, to suppress magnetic fields generated by the magnet, for safety and for inhibiting pellet formation during mixing. The magnet 121 may be formed of any magnetizable or naturally magnetic material, or combinations thereof.

An RFID tag 122 of the type known in the art may be attached to, or integrated in, the cartridge 120. When the cartridge 120 is brought close to the portable substance identification device 101, the RFID tag may be energized by RF energy provided by the communicator 105 to transmit data about the cartridge 120 to the portable substance identification device 101 for verification. The data about the cartridge 120, which is received by a processor 104, 162 of either the portable substance identification device 101 or an agitator 160 (FIGS. 1 and 17), can include, but is not limited to: a unique manufacturer identifier, an expiration date, a predetermined agitation cycle, a type of assay, and the like. After using the data about the cartridge 120 to determine that the cartridge was legitimately manufactured by an authorized source, and/or after using the data about the cartridge to determine that a perishable reagent within the cartridge 120 has not expired, and/or after using the data about the cartridge 120 to determine a type of assay to be performed, the processor 104 of the portable substance identification device 101 or the processor 162 of the agitator 160 may transmit, via a communicator 105 or other device, validation or other information to the cartridge 120. In one embodiment, the validation or other information is transmitted to an RFID tag 122 coupled with the cartridge 120.

The cartridge 120 may be disposable, but in another embodiment may be re-usable after the chamber 128 is cleansed and/or decontaminated using any known cleansing and/or decontamination technique. It will be appreciated that the type of cleansing and/or decontamination technique used will vary depending on the type(s) of reagent(s) used. For example, if a reagent targeting a benign type of detection target, such as an explosive, were used, the chamber 128 may be cleansed/decontaminated by washing with soap and water and/or by steam cleaning. On the other hand, if a reagent targeting a type of pathogen, such as anthrax, were used, other types of cleaning/decontamination techniques may have to be used. Examples may include irradiating the chamber 128 with an amount of radiation sufficient to neutralize the pathogen or coating the chamber with any substance that causes lysis—the dissolution or destruction of cells.

The Collection Stem

With continued reference to FIG. 1, the collection stem 140 may have any suitable shape. The material used to form the collection stem housing and/or subcomponents of the collection stem 140 may be, but is not limited to, plastic, polymers, metal, metal alloys, and combinations thereof.

A portion of the collection stem 140 that includes a collector 144 may be configured to be coupled with the chamber 128. In this document, the term "collector" refers to a portion 144 of the collection stem 140 that comprises a sterile collection device. A collection device can bean absorbent or non-absorbent material, such as a textile, fiber, or foam. The term "absorbent" is used in its normal sense to mean a material having capacity or tendency to absorb another substance. Examples of an absorbent textile, fiber, or foam include, but are not limited to, a piece of cotton, or knitted polyester material, and the like. Cotton may be used for microbiological sampling, and knit polyester may be used for chemical sampling. The term "non-absorbent" refers to a material that has no capacity or tendency to absorb another substance, but which has a surface configured to be wetted by the liquid medium, or other aqueous solution. Examples of a non-absorbent textile, fiber or foam include, but are not limited to, metal, polymer, plastic, nylon, and the like. In alternative embodiments, the collector 144 may include an electrostatically charged plate or a suction mechanism.

The collection stem 140 may include at least one reservoir that contains a liquid medium 141. Alternatively, the liquid medium 141 may be stored in the cartridge 120. The liquid medium 141 may be a buffer solution, such as phosphate buffered saline (PBS) (or other compatible type of liquid medium). The collection stem 140 may optionally include another reservoir that contains the at least one reagent 143.

One or more channels may couple the reservoir(s) of the collection stem 140 with the actuator 142 and/or with the collector 144. In one embodiment, an actuator 142 may be a plunger. A portion of the liquid medium 141 can be used to wet a collector 144 of the collection stem 140 so that the collector 144 more readily attaches to at least one detection target or to a substance that may contain the at least one detection target. In another embodiment, a dry collector 144 can be used to attach to at least one detection target or to the substance that may contain the at least one detection target.

Another portion of the collection stem 140 may include an actuator 142. In this document, the term "actuator" refers to any type of plug, or other type of plug-like device, that, in response to applied pressure, sealably slides within a bore of a chamber, channel, reservoir, cavity, or container to force air and/or liquid medium therefrom. The actuator 142 may be configured to express some, or all, of the liquid medium 141 through the collector 144 to sweep a detection target that may have been affixed to the collector 144 into the chamber 128 for mixing with the at least one reagent 143.

Agitator

Referring again to FIG. 1, the agitator 160 may have any suitable shape. The material used to form the agitator housing and/or subcomponents of the agitator 160 may be, but is not limited to, plastic, polymers, metal, metal alloys, and combinations thereof. The agitator 160 may be configured to enclose the cartridge 120 and/or the collection stem 140 fully or partially.

The agitator 160 may be configured to agitate the cartridge 120 and/or the collection stem 140 for a predetermined period of time to mix the at least one reagent 143, the liquid medium 141, and the at least one detection target—if any—within the chamber 128 until the at least one detection target—if any—binds to the at least one reagent 143 by affinity reaction.

The agitator 160 may include a display 167, a user interface 161, a power source 165, a computer processor 162, and a computer-readable memory 163, of the types known in the art. Each of these agitator components may be coupled with the others via electrical/digital circuitry such as bus 166.

The agitator 160 may be separate and distinct from the system's other components 101, 120, and 140. In one embodiment, the agitator 160 is a decontaminable, battery operated device configured to receive, and shake, the cartridge 120, which is engageable with and removable from the agitator 160. The agitator 160 can be decontaminated using bleach, radiation, or other disinfectant. In other embodiments, the agitator 160 may be incorporated within any of the components 101, 120, or 140. The exemplary agitator 160 shown in FIG. 1 is a machine. However, in an alternate embodiment, the cartridge 120 and/or the collection stem 140 may be shaken by hand. In an alternate embodiment, the agitator 160 can be a laboratory rocker.

Chamber

Figure 2:
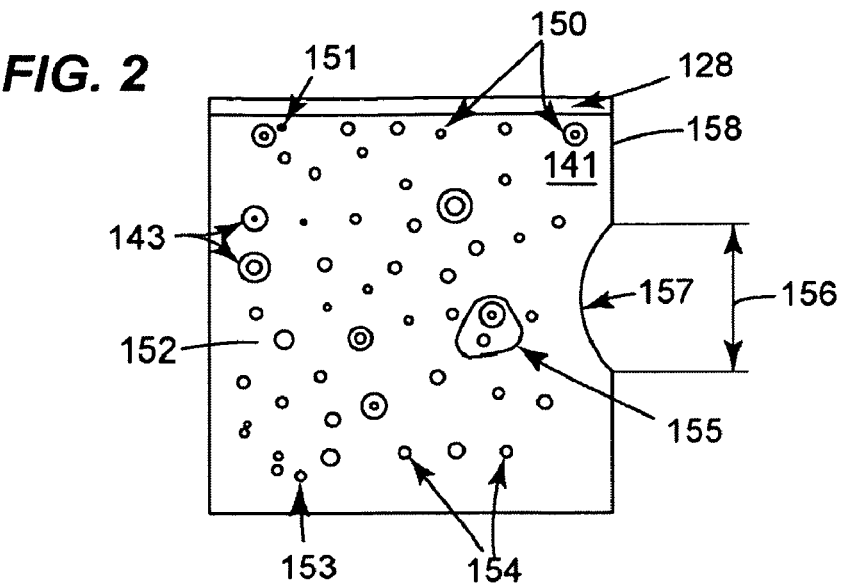
FIG. 2 is a schematic illustration of a chamber that may be used in an embodiment of the portable substance identification system of FIG. 1.

FIG. 2 is a schematic illustration of a chamber 128 that may be used in an embodiment of the portable substance identification system 100 of FIG. 1. The chamber 128 may have any suitable shape. For example, the chamber 128 may be generally circular in cross-section. In another embodiment, the chamber's cross-sectional diameter may vary along the chamber's length or height.

Figure 3:
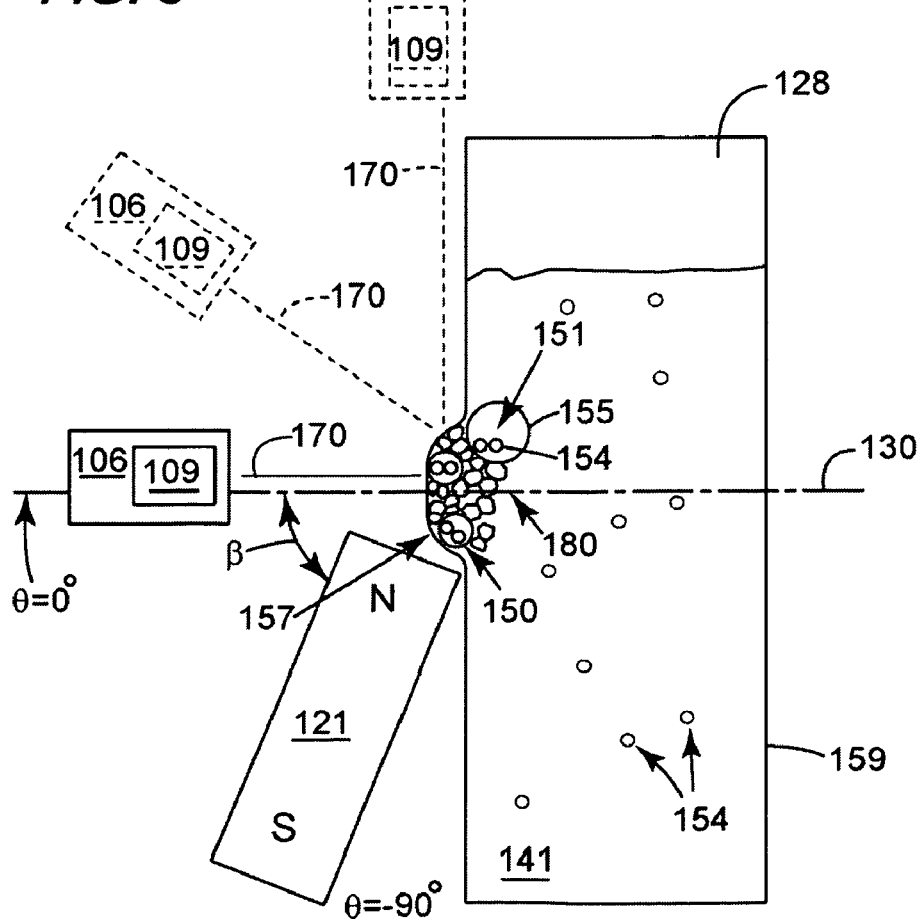
FIG. 3 is a schematic illustration of the chamber of FIG. 2 in which the chamber contains a liquid medium in which a pellet is magnetically formed.

In one embodiment, a portion of the material(s) forming the chamber 128, or forming a pellet forming area 156 (FIG. 3) of the chamber 128, are permeable by a laser beam 170 (FIG. 3). In particular, a portion of the material used to form the chamber 128, or used to form the pellet forming area 156, is an optically transparent material such as glass, plastic, and the like. The remainder of the material forming the cartridge 120 (FIGS. 8-31) is configured to block ambient light so that there is no optical interference with the Raman signal from the pellet when a laser beam is incident.

A wall of the chamber 128 may include a pellet forming area 156. A magnetic field or a magnetic field gradient may be exerted within the pellet forming area 156 when a magnet is suitably positioned proximate the wall 158. A portion of the wall 158 within the pellet forming area 156 may have a predetermined geometry 157. In an embodiment, the predetermined geometry 157 may be a specially shaped area of the chamber wall 158 that functions to allow formation of a pellet 180 having greater surface area than a non-specially shaped area of the chamber wall 158.

By way of example, and not limitation, a cross-sectional shape of the predetermined geometry 157 may be convex, concave, square, angular, and the like. The predetermined geometry 157 may protrude into a bore of the chamber 128, or may protrude externally from a body of the chamber 128.

The chamber 128 may be configured to contain a liquid medium 141 in which may be suspended multiple unbound first, second, third, and more types of detection targets 151, 152, 153, respectively, and at least one type of unbound reagents 143. It will be appreciated that a monoplex assay, a duplex assay, a triplex assay, or other multiple kinds of assays, can be performed depending on the number of types of detection targets 151, 152, 153 provided. For example, an assay can be performed using three or more types of detection targets 151, 152, 153. Regardless of the type or number of assays simultaneously performed, the binding process between the detection targets 151, 152, 153 and the one or more reagents 143, which can include the one or more optically responsive tags 154, is mediated by the detection targets 151, 152, 153 themselves.

Some non-limiting examples of an optically responsive tag 154 include a surface-enhanced Raman spectroscopy tag, a surface-enhanced resonant Raman spectroscopy tag, a fluorescent label, or a calorimetric tag. The different types of detection targets 151, 152, 153 may include living organisms and non-organic matter. Some non-limiting examples of detection targets 151, 152, 153 include prokaryotic cells, eukaryotic cells, bacteria, spores, viruses, proteins, polypeptides, toxins, liposomes, amino acids, and nucleic acids, either individually or in any combinations thereof. Other non-limiting examples of detection targets 151, 152, 153 include molecules of known explosives and/or molecules of known poisons, nerve agents, and the like.

Actuator and Reservoir Seal

Referring to FIGS. 8-28, an embodiment of an actuator 142 is coupled with one or more reservoirs 2010, 2602, and is configured to move relative to the reservoir(s) to which it is coupled. A seal 2006, 2603 disposed at an end of each reservoir 2010, 2602 is configured to rupture when the actuator 142 is moved relative to each reservoir 2010, 2602.

Magnet

FIG. 3 illustrates an advantageous apparatus for sampling a collected pellet 180 by shining a laser beam 170 onto the pellet 180 from a laser source 109. The pellet 180 may be formed by positioning a magnet 121, such as a bar magnet or other type of magnet, at a slant angle $\beta$ relative to the central axis 130. Orientating the magnet 121 at a slant angle $\beta$ is advantageous in that it permits the laser source 109 to be located on the same side of the chamber 128 as the magnet 121. This orientation may reduce or eliminate virtually all the problems associated with former spectroscopic apparatus and techniques, which position the laser source 109 on a side of the chamber 128 opposite the magnet 121.

In embodiment, the slant angle $\beta$ of the magnet 121 ranges from and includes about +80° to about −80°, including 0°, which is parallel the central axis 130 and orthogonal to a wall 158 of the chamber 128. The laser source 109 may be positioned at any angle $\theta$, in the range of about +90° to about −90°, with respect to a central axis 130 of the chamber 128.

In FIG. 3, a non-limiting, exemplary position of the spectrometer 106 and laser source 109 are indicated in solid lines at an angle $\theta$ of about 0°. Exemplary alternate positions of the spectrometer 106 and the laser source 109 are indicated in dotted lines at other angles $\theta$. A non-limiting, exemplary position of the magnet 121 is indicated in solid lines at an angle $\beta$ of about 45°, relative to the central axis 130.

Alternate positions of the magnet 121 are possible, but are not shown so as not to over complicate the drawing. For example, the magnet 121 may be positioned at a slant angle $\beta$ that is orthogonal to a wall 158 of the chamber 128 (See FIG. 6). With the magnet 121 so positioned, the laser source 109 can be positioned at angle $\theta$ with respect to the central axis 130, wherein the angle $\theta$ is non-orthogonal to the wall 158 of the chamber 128. Alternatively, if a bore is formed in the magnet 121, the laser source 109 and the magnet 121 can be positioned so that the slant angle $\beta$ of the magnet 121 and the angle $\theta$ of the laser source 109 are each orthogonal to the wall 158 of the chamber 128. In such a configuration, the magnet 121 is positioned between the laser source 109 and the pellet forming area 156 of the chamber 128, and the laser beam 170 is projected through the bore of the magnet 121 (See FIGS. 4 and 5).

In operation, a magnetic field produced by the magnet 121, which is positioned proximate the predetermined geometry 157 of the chamber wall 158, clusters the magnetic particles 150 and/or at least one group of tagged detection targets 155 into a pellet 180. Force exerted by the magnetic field, or the magnetic field gradient, of the magnet 121 presses the pellet 180 onto the predetermined geometry 157 of the chamber wall 158, causing the pellet 180 to have more surface area than it would if the pellet 180 were simply pressed against a flat container wall 158. Because the predetermined geometry 157 increases the pellet's surface area, the ratio of the pellet's surface area to its volume is increased.

Spectrometer and Laser Source

Referring to FIG. 3, the laser beam 170 used to scan the pellet 180 may be produced by a laser source 109 positioned on the same side of the container wall 158 as the magnet 121. To prevent overheating, the pellet 180 may be scanned without first evacuating the liquid medium 141 from the chamber 128. Additionally, or alternatively, the laser beam 170 may be dithered using known techniques.

The laser source 109 may be a component of a Raman spectrometer 106, which may further include a detector for detecting laser light scattered from the pellet 180, as well as circuitry, a computer processor, a computer-readable memory, and software stored in the memory that are configured to analyze the electrical/digital outputs of the detector to identify at least one detection target (if present in the pellet 180).

Exemplary Magnet, Pellet, and Chamber Configurations

FIGS. 4, 5, 6, and 7 are unscaled diagrams of exemplary magnet, pellet, and reaction chamber configurations 400, 500, 600, and 700 that may be practiced in accordance with at least one embodiment of the claimed invention. Any of these configurations 400, 500, 600, and 700, or modifications thereof, may be used in the portable detection device 101 or the cartridge 120, which are illustratively shown in FIG. 1. For ease of illustration, and to more clearly show the laser beam 170 emitted by the laser source 109, the Raman spectrometer 106 of FIGS. 1 and 2 is omitted from FIGS. 4, 5, 6, 7.

Figure 4:
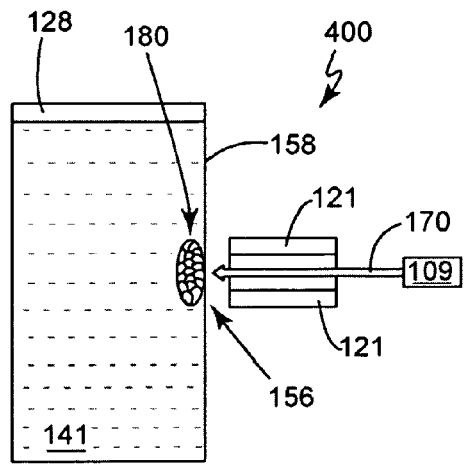
FIGS. 4, 5, 6, 7 are each unscaled diagrams of exemplary magnet, pellet, and reaction chamber configurations that may be practiced in accordance with at least one embodiment of the claimed invention.
Figure 5:
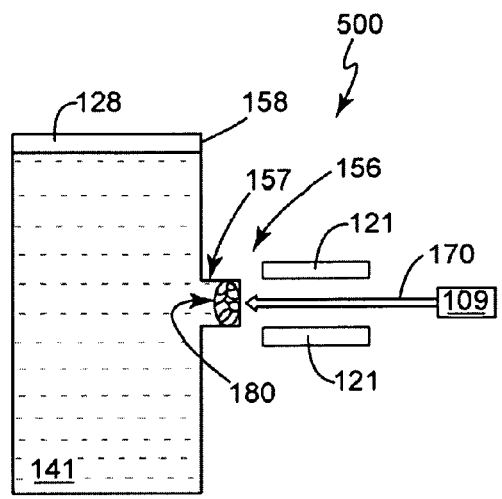

FIGS. 4 and 5 are each side views of a reaction chamber 128 having a liquid medium 141. One or more magnets 121 may be positioned on one side of the chamber 128, proximate a pellet forming area 156 of the chamber wall 158, to form a pellet 180 of aggregated magnetic particles, to which at least one other type of reagent can be attached. The at least one other type of reagent can include a perishable reagent, and/or at least one optically responsive tag. FIG. 4 illustrates that a laser source 109 positioned behind a single, hollow magnet 121 may shine a laser beam 170 through a bore of the magnet 121 to scan the pellet 180. FIG. 5 illustrates that a laser source 109 positioned behind two spaced-apart, parallel magnets 121 may shine a laser beam 170 between the magnets 121 to scan the pellet 180.

In FIG. 4, the pellet 180 is shown as being formed against a smooth wall 158 of the reaction chamber 128. In FIG. 5, the pellet 180 is shown as being formed inside a predetermined geometry 157, which protrudes outwardly from the wall 158 of the chamber 128.

Figure 6:
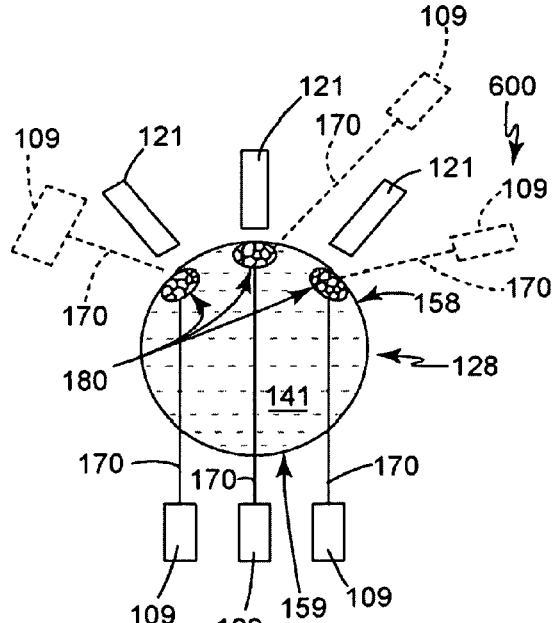
Figure 7:
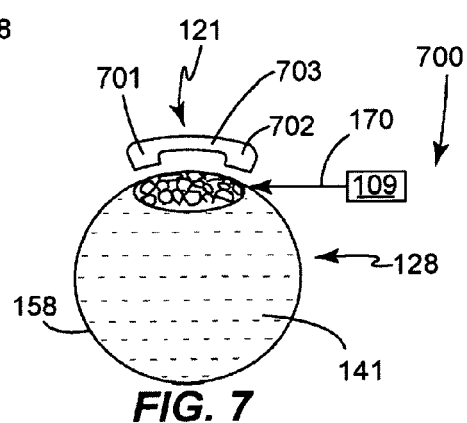

FIGS. 6 and 7 are top views of a chamber 128 containing a liquid medium 141. FIG. 6 illustrates how multiple magnets 121 may be positioned adjacent a wall 158 of the chamber 128 to form multiple pellets to form multiple pellets 180. FIG. 6 also illustrates that one or more laser sources 109, shown in solid lines, may be positioned on a side of the chamber 158 opposite the magnets 121 to direct a corresponding number of laser beams 170 through the chamber wall 159 and through the liquid medium 141 to scan each of the pellets 180. FIG. 6 further illustrates that one or more laser sources 109, shown in dotted lines, may be alternatively positioned on the same side of the chamber 128 as the magnets 121 to direct a corresponding number of laser beams through the chamber wall 158 to scan each of the pellets 180. The embodiment of the chamber 128 shown in FIG. 6 may be modified to include one or more predetermined geometries (157 in FIG. 5). To prevent optical interference, the multiple laser beams 170 may be emitted sequentially and/or at different wavelengths/frequencies.

FIG. 7 illustrates that a specially shaped magnet 121, positioned proximate the chamber 128, may be used to form a pellet 180 having a maximized ratio of surface area to volume along a smooth portion of the chamber wall 158. As illustratively shown, each end 701, 702 of the magnet 121 may have a cross-sectional thickness that is greater than a cross-sectional thickness of a middle section 703 of the magnet 121.

Exemplary Portable Substance Identification Systems

Figure 8:
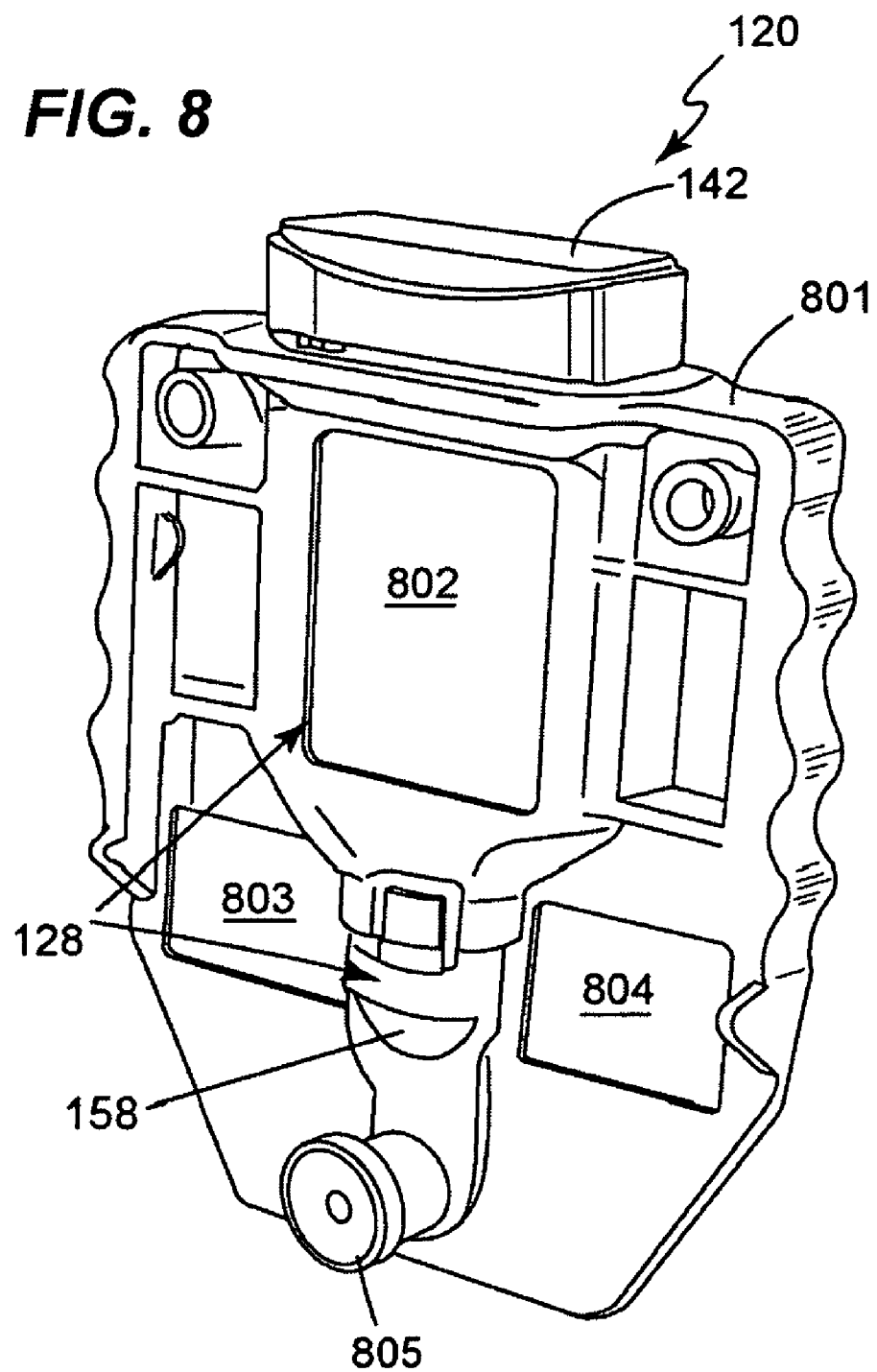
FIG. 8 is a perspective view of an embodiment of a cartridge that may be used in an embodiment of the portable substance identification system of FIG. 1.

FIG. 8 is a perspective view of an embodiment of a cartridge 120. FIG. 9 is a top view of the cartridge 120 of FIG. 8. FIG. 10 is a front view of the cartridge 120 of FIG. 8. FIG. 11 is a side view of the cartridge 120 of FIG. 8.

Referring to FIGS. 1, 3, 8, 9, 10, and 11, the cartridge 120 may be used together with a collection stem 140, the portable substance detection device 101, and/or the agitator 160 to analyze and identify at least one detection target that is collected on a collector 144 of the collection stem 140. The body, or housing, 801 of the cartridge 120 may have a blunt top end and tapered bottom end; and the sides of the body 801 of the cartridge 120 may be configured to provide a non-slip gripping surface. A actuator 142 of a collection stem 140 may extend past the blunt top end of the housing 801 when the collection stem 140 is inserted within a chamber of the cartridge 120. A hand or machine operated actuator 805 may protrude from a portion of the tapered bottom end of the cartridge 120. The actuator 805 may be configured to move the magnet 121 toward or away from a wall 158 of the chamber 128. A pellet 180 may form when the magnet 121 is moved toward the wall 158.

Portions 802, 803, and 804 of the cartridge housing 801, and portions 806 and 807 of the actuator 142, may include any suitable indicia. Examples of indicia include but are not limited to the name and/or logo of a manufacturer of the cartridge; the names and/or type(s) of detection target(s) the cartridge, and/or the collection stem 140, are configured to identify; an expiration date of the cartridge, and/or the collection stem 140; and so forth. Additionally, or alternatively, the portions 802, 803, 804, 806, and 807 may include at least one of an RFID tag 122 and a cartridge display 129.

Figure 13:
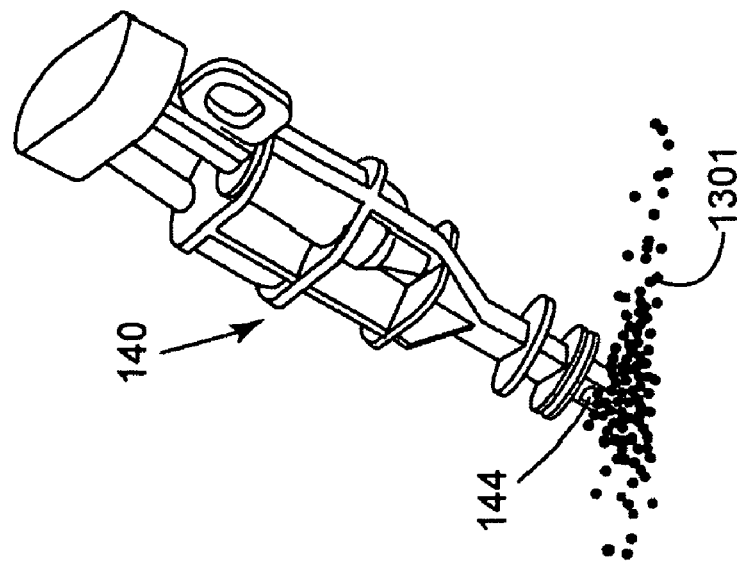
FIG. 13 is a side perspective view of an embodiment of the collection stem of FIG. 12.
Figure 12:
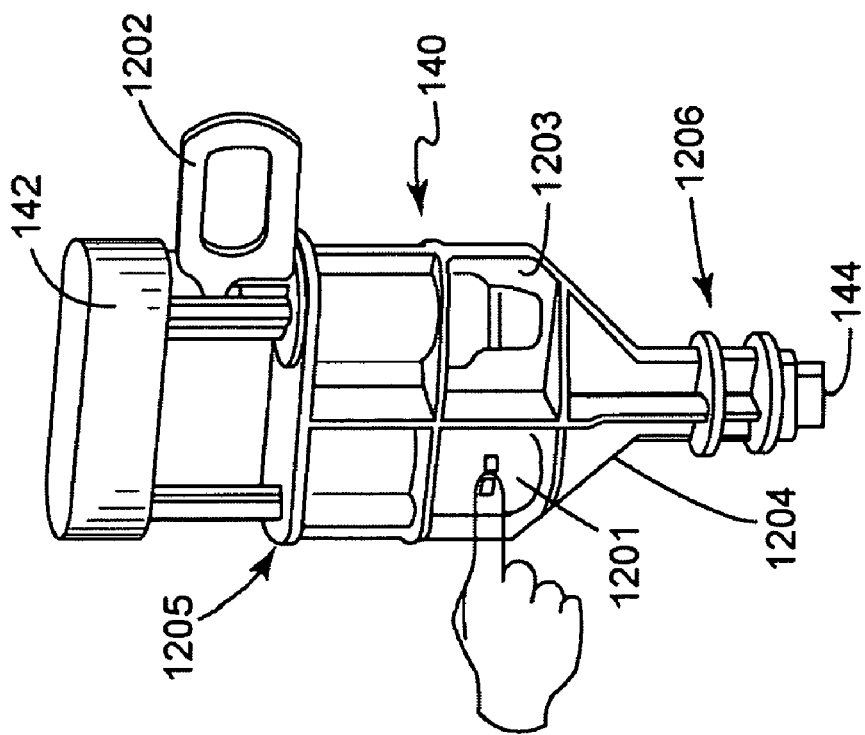
FIG. 12 is a front perspective view of an embodiment of a collection stem that may be used in an embodiment of the portable substance identification system of FIG. 1.

FIG. 12 is a front perspective view of an embodiment of a collection stem 140. FIG. 13 is a side perspective view of an embodiment of the collection stem 140 of FIG. 12. Referring to FIGS. 12 and 13, a collection stem 140 may include a sealed housing 1203. A actuator 142 may protrude from one end 1205 of the collection stem housing 1203. To prevent the actuator 142 from being depressed accidentally, a locking mechanism 1202 may be detachably coupled to a portion of the actuator 142. In one embodiment, the locking mechanism 1202 may be interposed between a handle of the actuator 142 and an end 1205 of the collection stem housing 1203. However, other types of locking devices/mechanisms may be implemented in other embodiments to prevent the actuator 142 from being engaged accidentally.

The collection stem housing 1203 may include a button 1201. The button 1201 may be may be any mechanism coupled with a sealed vessel, that functions to rupture the sealed vessel in response to pressure applied by, or in response to other input from, a user of the substance detection system. Alternatively, the button 1201 may comprise a portion of the sealed vessel. In an embodiment, the sealed vessel may be an object, formed of a rupturable material, that contains, or is configured to contain, a liquid medium. Non-limiting examples of a rupturable material include, but are not limited to, glass, plastic, polymer, metal foil, or combinations thereof, and the like.

The button 1201 can be formed of a material having flexible or rigid properties and may be protected from accidental engagement by at least one rib 1204, or other type of protective member, such as a substrate or lid formed of plastic, metal, glass, or any combination thereof. In addition to protecting the button 1201 from being accidentally engaged, the at least one rib 1204 may structurally support the collection stem housing 1203. The button 1201 may also be protected from accidental engagement by a cover, by making the material that forms the button 1201 to have a predetermined depression pressure, and/or by making the material that forms the sealed vessel (not shown in FIG. 12) positioned under the button 1051 to have a predetermined breaking pressure. The sealed vessel, containing a first quantity of liquid medium and formed within the collection stem housing 1203, may rupture when external pressure is applied to the button 1201. An exemplary sealed vessel 2007 is shown in and described with reference to FIG. 20.

Referring still to FIGS. 12 and 13, a collector 144 may protrude from an opposite end 1206 of the collection stem housing 1203. In one embodiment, the end 1206 of the collection stem housing 1203 may be smaller than the end 1205 of the collection stem housing 1203. A porous, absorbent, sterile material may form the collector 144. The collector 144 may be configured to collect a sample substance 1301 for Raman-spectroscopic analysis. The collected sample substance 1301 may contain at least one detection target.

Figure 16:
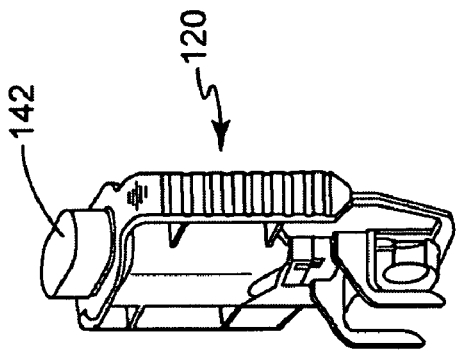
FIGS. 14, 15, and 16 are side perspective views of an embodiment of the cartridge of FIGS. 1, 8, 9, 10, 11, and 12 that illustrate how an embodiment of the collection stem of FIGS. 12 and 13 may be slidably and sealably engaged within a chamber of the cartridge.
Figure 15:
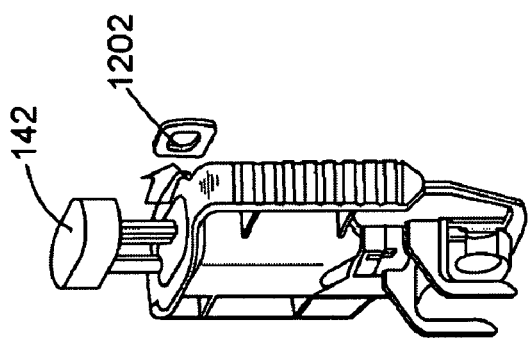
Figure 14:
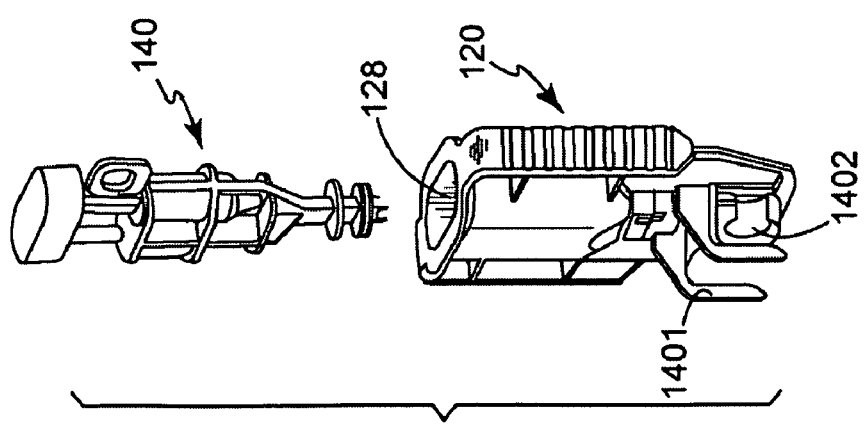

FIGS. 14, 15, and 16 are side perspective views of an embodiment of a cartridge 120 that illustrate how an embodiment of a collection stem 140 may slidably and sealably engage within a chamber 128 of the cartridge 120.

In an embodiment, the collection stem 140 may not be removed once it is fully inserted into the chamber 128. In such an embodiment, the collection stem 140 and the cartridge 120 may be shipped in individually sealed packages.

In another embodiment, the collection stem 140 may be removed from the chamber 128 provided it is not fully inserted into the chamber 128 when the actuator 142 is depressed. In such an embodiment, the collection stem 140 may be packaged with the locking mechanism 140 attached to the actuator 142 and with the collection stem 140 stored inside the chamber 128 of the cartridge 120.

FIG. 14 further shows that an embodiment of the pellet forming area 156 (FIG. 3) of the chamber 128 of the cartridge 120 is a sampling window 1402 on which at least one pellet may be formed by the magnet 121, which may be held and/or moved and/or energized by movement of the actuator 805. In an embodiment, the sampling window 1402 may be integrated with and/or form part of the wall 158 (see FIGS. 2, 3). The cartridge 120 can be configured to couple with a portable substance identification device 101 to align the pellet forming area 156 with a laser source 109 (FIG. 3), which can be positioned on a same side of the pellet forming area 156 as the magnet 121. The magnet 121 can be included in either the cartridge 120 or in the portable substance identification device 101.

Referring to FIGS. 1, 3, 14, 15, and 16, the cartridge 120 may include at least one attachment member 1401. The at least one attachment member may be configured to removably engage a portable substance identification device 101 and/or configured to align the pellet forming area 156 (FIG. 3) of the chamber 128 with a laser beam of a Raman spectrometer 106. In one embodiment, the Raman spectrometer 106 is located in the portable substance identification device 101. A pronged embodiment of attachment members 1401, configured to slidably engage a rim of a portable substance detection device 101, is shown in FIGS. 14, 15, and 16; but other types of attachment members 1401 are within the scope of the claimed invention.

Figure 17:
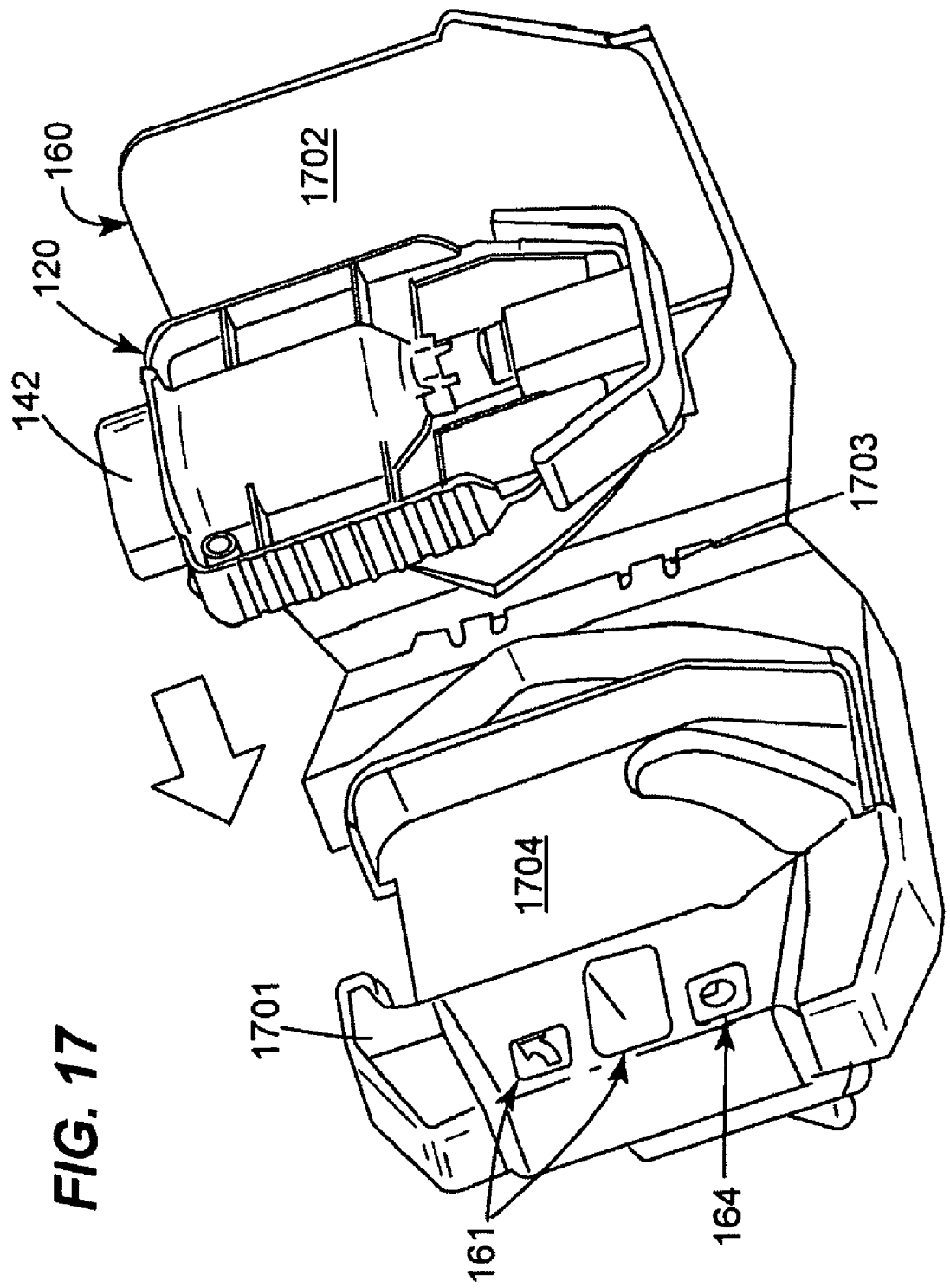
FIG. 17 is a front perspective view of an agitator device that may be used in an embodiment of the portable substance identification system of FIG. 1.

FIG. 17 is a front perspective view of an agitator device 160 illustrating how a cartridge 120, with a collection stem 140 therein and an actuator 142 depressed, can be placed within a receptacle 1704 formed within a body 1701 of the agitator device 160. At least one connector 1703 may couple the body 1701 of the agitator device 160 with a cover 1702. When closed, the cover 1702 may secure a cartridge 120 within the receptacle 1704. Other embodiments may include other means of securing the cartridge 120 to the agitator 160.

A portion of the body 1701 of the agitator device 160 may house a user interface 161, a mixer 168 (in FIG. 1), and/or a timer 164. The agitator device 160 may also include audio and/or visual means for signaling the expiration of an agitation cycle. In an embodiment, an agitation cycle may range from multiple seconds to multiple minutes.

Figure 18:
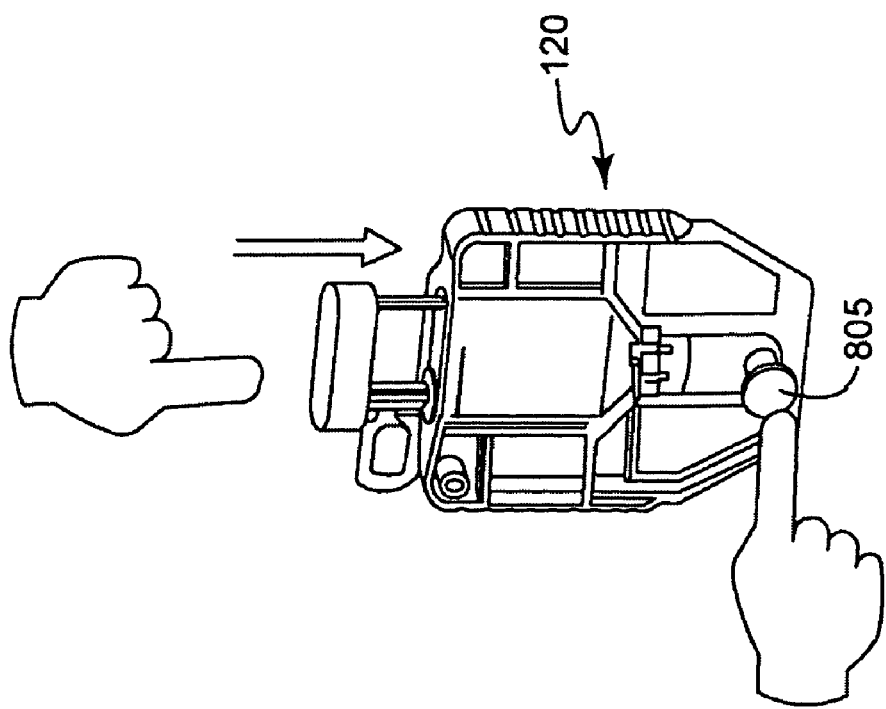
FIG. 18 is a front perspective view of the cartridge of FIGS. 1, 8, 9, 10, 11, and 12 illustrating how an actuator positioned on an exterior portion of the cartridge may be engaged to cause at least one magnet to create at least one pellet within a reaction chamber.

FIG. 18 is a front perspective view of a cartridge 120 illustrating how an actuator 805 positioned on an exterior portion of the cartridge 120 may be engaged to cause at least one magnet to create at least one pellet within a reaction chamber.

Figure 19:
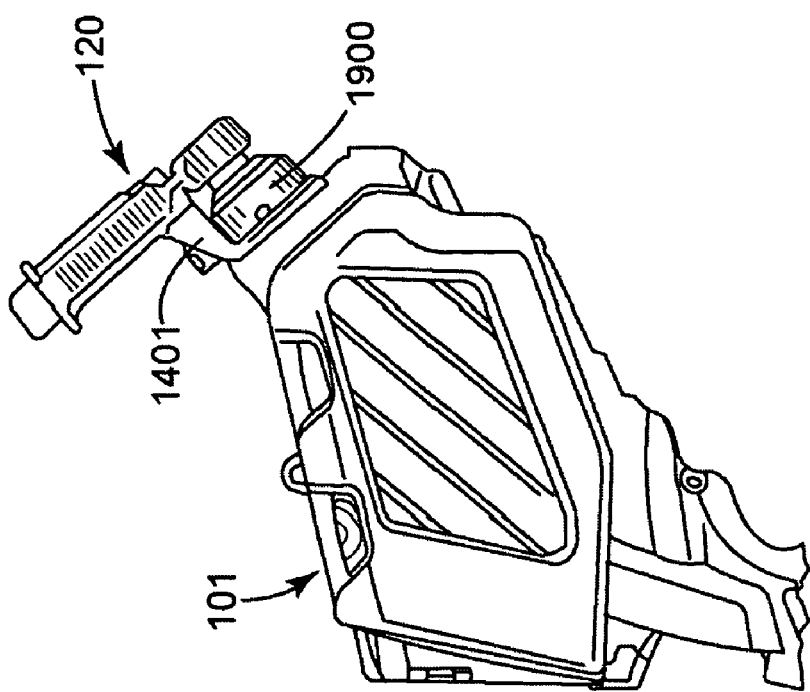
FIG. 19 is a side view of an embodiment of a portable substance identification device and an embodiment of a cartridge removably coupled thereto that may be used in an embodiment of the portable substance identification system of FIG. 1.

FIG. 19 is a side view of an embodiment of a portable substance identification device 101 and an embodiment of a cartridge 120 removably coupled thereto. An exterior rim 1900 of the portable substance identification device 101 may be configured to slidably engage the at least one attachment member 1401. When mounted on the portable substance identification device 101 as shown, a pellet forming area (not shown in FIG. 19) of a reaction chamber may be positioned for interrogation and analysis by a laser beam emitted from a Raman spectrometer contained in the portable substance identification device 101.

Viewed together, FIGS. 12, 13, 14, 15, 16, 17, 18, and 19 illustrate a method of collecting and identifying at least one detection target. The method may begin at FIG. 12 when a collection stem 140 is removed from a sealed package. The sealed package may include traditional plastic/foil packaging materials and/or may include a chamber 128 of the cartridge 120. As FIG. 12, illustrates, pressure may be applied to the button 1201 to wet the collector 144 with a quantity of liquid medium. In an alternative embodiment, the collector 144 may be applied to a target substance without first being wetted.

Next, as shown in FIG. 13, the wetted collector 144 may be contacted with a sample substance 1301. Wetting the collector 144 makes collecting molecules of a sample substance 1301 easier, ensures that a sufficient amount of the sample substance 1301 is collected, and minimizes the number of particles that may become airborne when the collector 144 is pressed into a powdered sample substance 1301. The sample substance 1301 may be in the form of a liquid, a powder, a solid, or a vapor.

Proceeding to FIG. 14, the collection stem 140, with some of the sample substance 1301 attached to the collector 144, may be inserted within a chamber 128 of a cartridge 120. Optionally, at this step, the collection stem 140 may be secured within the chamber 128.

Proceeding to FIG. 15, once the collection stem 140 has been slid within the chamber 128 of the cartridge 120, the locking mechanism 1202 may be removed from the actuator 142.

Proceeding to FIG. 16, and also referring to FIGS. 2 and 3, once the locking mechanism 1202 has been removed, the actuator 142 may be depressed, or activated. A liquid medium 141 and/or a plurality of magnetic and optically responsive reagents 143 may be expressed into the reaction chamber 128, together with any detection targets 151, 152, 153 that formed part of the collected sample substance, as the actuator 142 is activated.

Proceeding to FIG. 17, with reference to FIG. 1, any such detection targets 151, 152, 153 may be mixed via agitation with the at least one reagent 143. Agitation, which may be provided by the mixer 168 of the agitator 160, may occur by hand, by a mechanical device, by an electromechanical device, by magnetic device, by an electromagnetic device, by chemical reaction, by a suitably designed flow path in the cartridge and the like. In one embodiment, the cartridge 120 containing a collection stem 140 with its actuator 142 depressed may be removably inserted within a receptacle 1704 formed in a body 1701 of an agitator 160. Thereafter, the cartridge 120 may be secured to the agitator 160, for example by closing a cover 1702 of the agitation device. A user interface 161 may be used to program and activate a timer 164. Once the timer 164 is activated, the mixer 168 of the agitator 160 may agitate, in any known manner, the liquid medium 141 and any detection targets 151, 152, 153 and reagents 143 contained therein. When the timed period of agitation expires, the cartridge 120 may be removed from the agitator 160. If the cartridge 120 is equipped with a radio frequency identification tag, or with a transmitter, a processor in the agitator 160 can receive and process data from the cartridge 120, such as an expiration date, a predetermined agitation cycle, unique manufacturer identifier, or other data. The data received from the cartridge 120 and/or processed data output by the processor can be stored in a memory of the agitator 160, which is coupled with the processor of the agitator 160. In one embodiment, data stored in the memory of the agitator 160, and/or processed data output by the processor of the agitator 160, can be transmitted to the cartridge 120.

Referring to FIG. 18, and also to FIGS. 2 and 3, following a predetermined period of time of agitation, an actuator 805 may be used to bring a magnet 121 near a pellet forming area 156 of a wall 158 of the chamber 128. In an embodiment, the actuator 805 may be engaged by hand. In another embodiment, the actuator 805 may be engaged other than by hand, for example via mechanical or electromechanical means.

Referring to FIG. 19, and also to FIGS. 2 and 3, the cartridge 120 may be removably coupled with the portable substance identification device 101 before or after the magnet 121 is brought near the pellet forming area 156. After the cartridge 120 is coupled with the portable substance identification device 101, the pellet formed by the magnet 121 may be scanned and/or analyzed using a laser beam 170 supplied by a Raman spectrometer 106. Using principles of Raman spectroscopy, at least one detection target 151, 152, 153 that has adhered to the at least one reagent 143, may be identified if the at least one detection target 151, 152, 153 is indeed present in the collected sample 1301. It should be noted, however, that if the liquid medium contains at least one magnetic particle, a pellet will always form in the presence of a magnetic field applied to the pellet forming area of the chamber, regardless of whether a detection target is present or not.

If a detection target is present, then it will bind to the reagent-coated, at least one magnetic particle and to a SERS, or other type of, tag. This binding is target-sensitive. So shining a laser beam 170 on the pellet will result in a SERS emission only if the detection target is present, because the detection target is needed to associate a SERS, or other type of tag, with the magnetic particle.

The results of the laser-based Raman spectroscopy may be displayed on a display device 110 of the portable substance identification device 101 and/or stored in a computer readable memory 104 associated therewith. Thereafter, the cartridge 120 may be removed from the portable substance identification device 101.

To ensure accuracy, the method may include validating the laser scan of the pellet. The validation, may include removing the cartridge 120 from the portable substance identification device 101, agitating the cartridge for a predetermined period of time, reforming a pellet, re-attaching the cartridge 120 to the portable substance identification device, re-scanning the pellet with the laser beam, identifying the detection target, if any, and displaying and/or storing the results of the validation.

Additionally or alternatively, the validation may include removing the magnet from the pellet forming area of the chamber, dispersing the magnetic particles by agitating the chamber, adding into the liquid medium a known or surrogate detection target, reforming a pellet, re-scanning the pellet with the laser beam, identifying the known or surrogate detection target, and displaying and/or storing the results of the validation. The method may further include displaying the validation results on a display device 109 of the portable substance identification device 101 and/or stored in a computer readable memory 104 associated therewith.

FIG. 20 is a front sectional view of a cartridge 120 having a chamber 128 configured to engage a collection stem 140 inserted therein. FIG. 21 is a side sectional view of the cartridge 120 and collection stem 140 of FIG. 20. Referring to both FIGS. 20 and 21, the cartridge 120 may include a magnet holder 2013 and a magnet 121 at its tapered end. A tapered end of the chamber 128 may include a pellet forming area 156, within which a pellet of tagged magnetic particles may be formed when the magnet 121 is suitably positioned and/or electrically powered. The tapered end of the chamber 128 may also include at least one reagent 2014 (143 in FIGS. 2 and 3).

A portion of the cartridge housing 801 that forms the chamber 128 may be configured to secure the collection stem 140 within the chamber 128. In one embodiment, a blocking member 2004 is formed on an end 1206 of the collection stem 140 and configured to engage a retaining member 2003 that forms part of the walls of the chamber 128. An o-ring seal 2005 may be included on the end 1206 of the collection stem 140 between the collector 144 and the rim 2004. The o-ring seal 2005 may engage the walls of the chamber 128 to prevent any liquid medium from exiting the chamber 128.

Referring still to FIGS. 20 and 21, a collection stem 140 may include a actuator 142 having a actuator guide 2001 and a actuator stem 2002. The actuator guide 2001 may slidably fit within a guide channel 2016 formed within the collection stem housing 2012. The actuator stem 2002 may slidably fit within a bore 2008 formed within a reservoir 2010. The bore 2008 may contain a liquid medium (141 in FIGS. 2 and 3). The reservoir 2010 may be fitted within a second channel 2015. An o-ring 2011 may be disposed about an exterior of the reservoir 2010 to engage the walls of a channel 2015, which opens into the chamber 128. A seal 2006, such as foil seal, is disposed at an end of the reservoir 2010 is configured to retain the contents of the reservoir 2010 within the bore 2008 until the actuator 142 is depressed by a user. Pressure exerted on the contents of the reservoir 2010 as the actuator 142 is depressed will cause the seal 2006 to rupture, thereby permitting the contents of the reservoir 2010 to pass through the channel 2015 and into the chamber 128.

The collection stem 140 may further include a sealed vessel 2007 disposed within a first channel 2009. The sealed vessel 2007 may be formed of a breakable material, and may include a first quantity of liquid medium (141 in FIGS. 2 and 3). As noted below, the sealed bore 2008 may contain a second quantity of the liquid medium.

The collection stem 140 may further include a collector 144 at its tapered end 1206. The collector 144 may be coupled with both the second channel 2015 and the first channel 2009. A portion of the collector 144 may extend within a portion of either the second channel 2015 or the first channel 2009.

Figure 22:
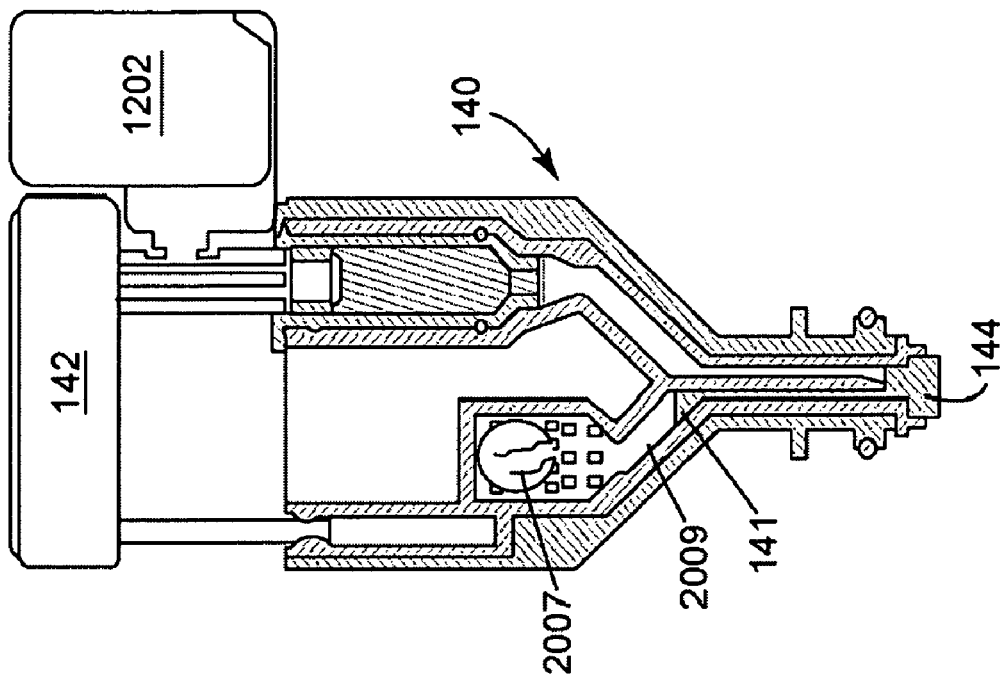
FIGS. 22, 23, and 24 are sectional views of an embodiment of the collection stem of FIGS. 13, 20, and 21.
Figure 23:
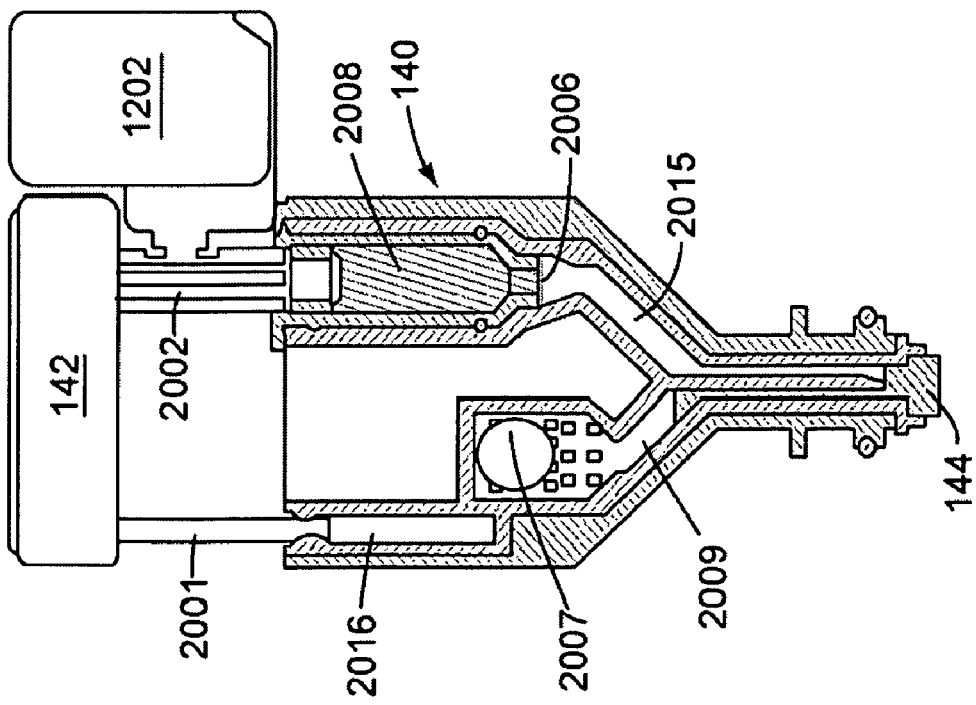
Figure 24:
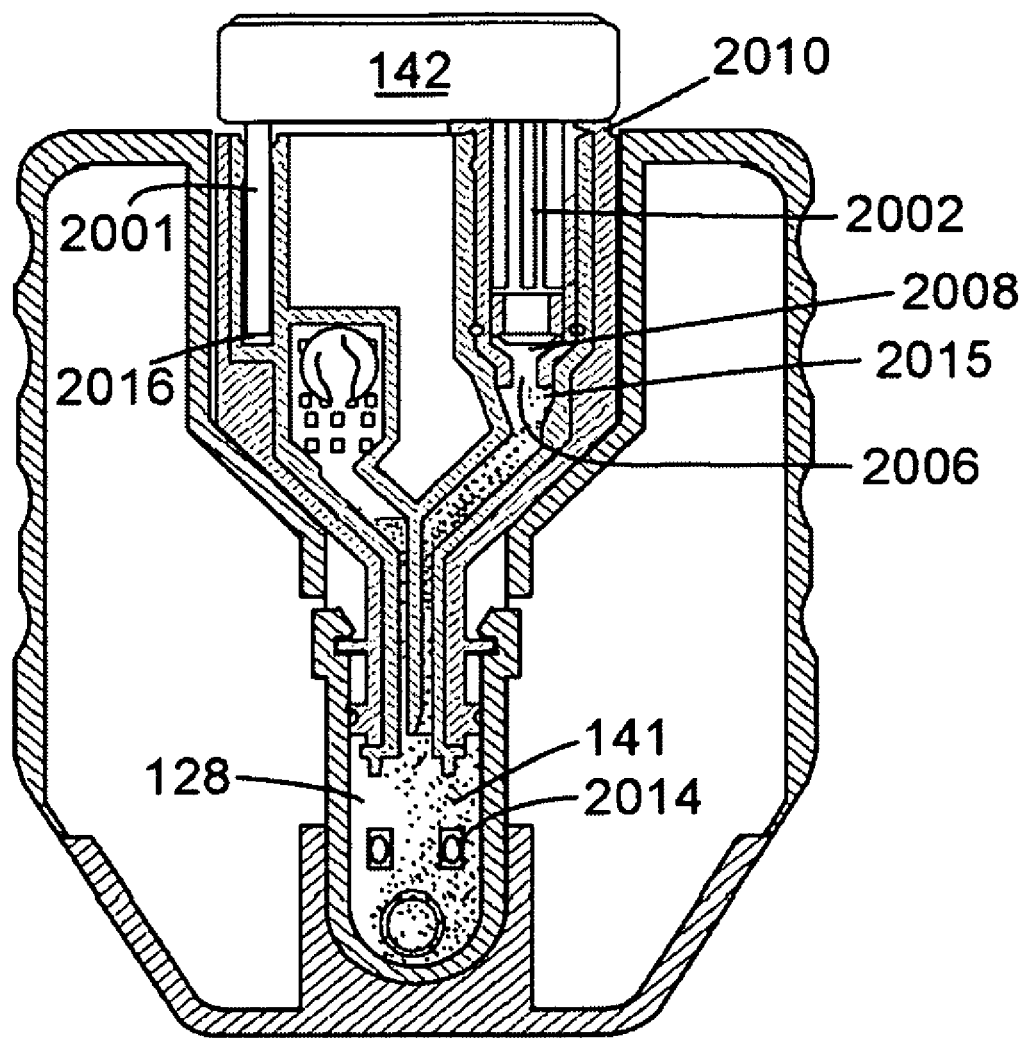

FIGS. 22, 23, and 24 are sectional views of an embodiment of a collection stem 140. Taken together, FIGS. 22, 23, and 24 illustrate how an embodiment of the collection stem 140 may operate. In FIGS. 22 and 23, the locking mechanism 1202 has not yet been removed from the actuator 142. Consequently, the actuator guide 2001 remains at an entrance of the guide channel 2016, and the actuator stem 2002 remains at an entrance of the bore 2008. Consequently, the bore 2008 retains its liquid medium and the reservoir seal 2006 remains intact. In FIG. 22, because an intact sealed vessel 2007 retains its liquid medium, the collector 144 remains dry.

In FIG. 23, a broken sealed vessel 2007 expresses its liquid medium along the first channel 2009, where the liquid medium contacts and is absorbed by the material that forms the collector 144. Thereafter, the wetted collector 144 may be contacted with a sample substance (1301 in FIG. 13).

In FIG. 24, the locking mechanism 1202 has been removed from the actuator 142, and the actuator 142 has been depressed. Consequently, the actuator guide 2001 is substantially inserted within the guide channel 2016, and the actuator stem 2002 is substantially inserted within the bore 2008. As the actuator stem 2002 moves along the bore 2008, pressure builds within the bore 2008 until the reservoir seal 2006 bursts and the liquid medium 141 contained in bore 2008 expresses into the second channel 2015, through the collector 144, and into the chamber 128, where it mixes with the at least one reagent 143. In this manner, activating the actuator 142 fills a reaction portion of the chamber 128 with liquid medium while simultaneously displacing the collected sample from the collector 144. Thereafter, the expressed liquid medium 141 may be agitated as described above. Following agitation, a magnet 121 may be used to form at least one pellet in a pellet forming area of the chamber 128.

Figure 25:
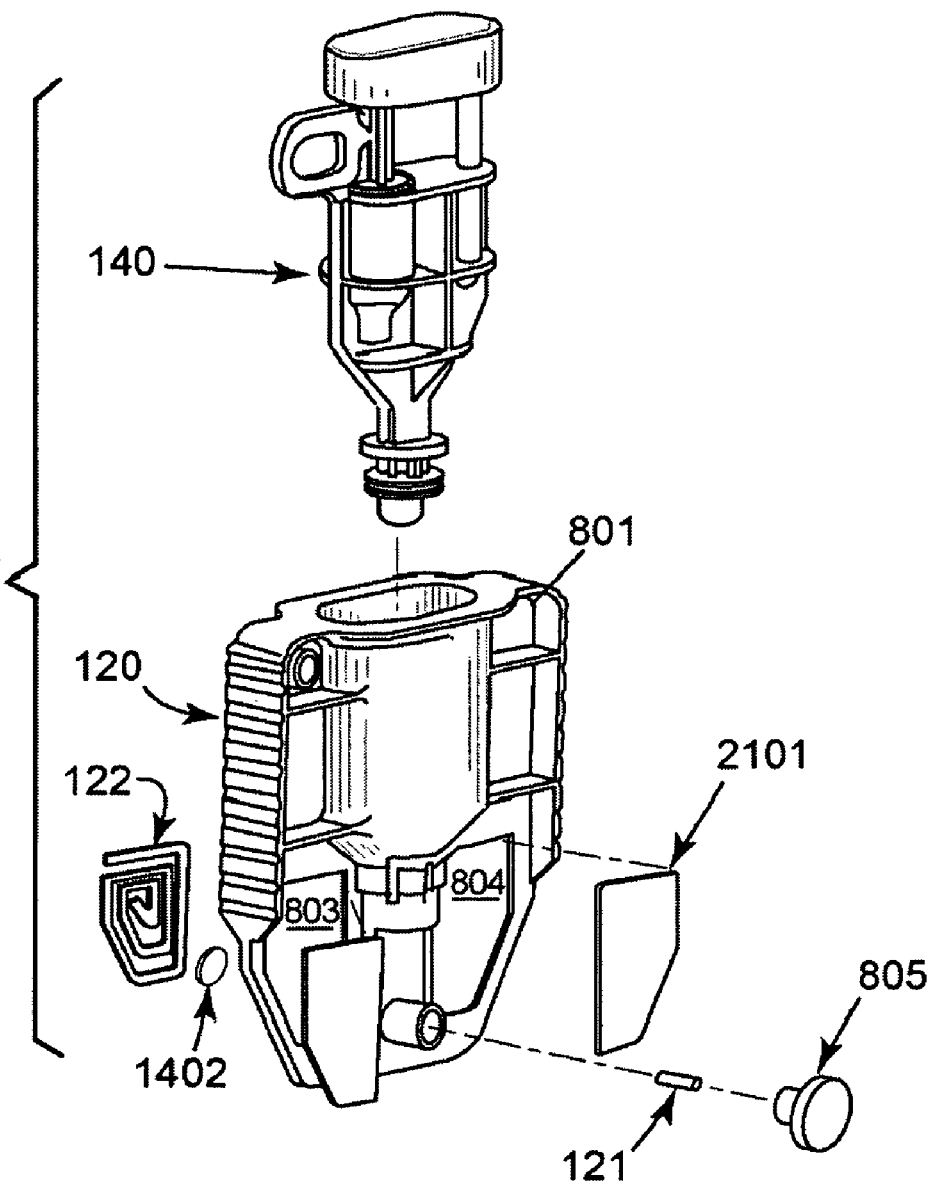
FIG. 25 is an exploded perspective view of an embodiment of the cartridge and the collection stem of FIGS. 13, 20, 21, 22, 23, and 24.

FIG. 25 is an exploded perspective view of an embodiment of the cartridge 120 and the collection stem 140 of FIGS. 1, 8, 9, 10, 11, 12, 13, 14, 15, 16, 17, 18, 19, 20, 21, 22, 23, and 24. As shown in FIG. 25, cartridge labels 2101 may be applied to a first surface of portions 803 and 804 of the cartridge housing 801. The cartridge labels 2101 may include information about the reagent(s) contained in the cartridge 120. An RFID tag 122 may be attached to a second opposite surface of either the portion 803 or the portion 804 of the cartridge housing 801. As previously described the RFID tag 122 can be configured to transmit data about the cartridge 120 to an agitator 160 and/or to a portable substance identification device 101. The transmitted data about the cartridge 120 may include, but is not limited to: a unique manufacturer identifier, an expiration date, a predetermined agitation cycle, and the like. The agitator 160 and/or the portable substance identification device 101 can be configured to operate or become temporarily inoperable, depending on whether the transmitted data about the cartridge is valid and/or has lapsed. As an alternative to the RFID tag 122, the cartridge 120 may include a processor, or microcontroller, coupled with a memory, a power source, and a wireless transceiver.

FIGS. 26, 27, 28, 29, 30, 31, and 32 are diagrams illustrating other embodiments of the apparatus and methods described above.

Figure 26:
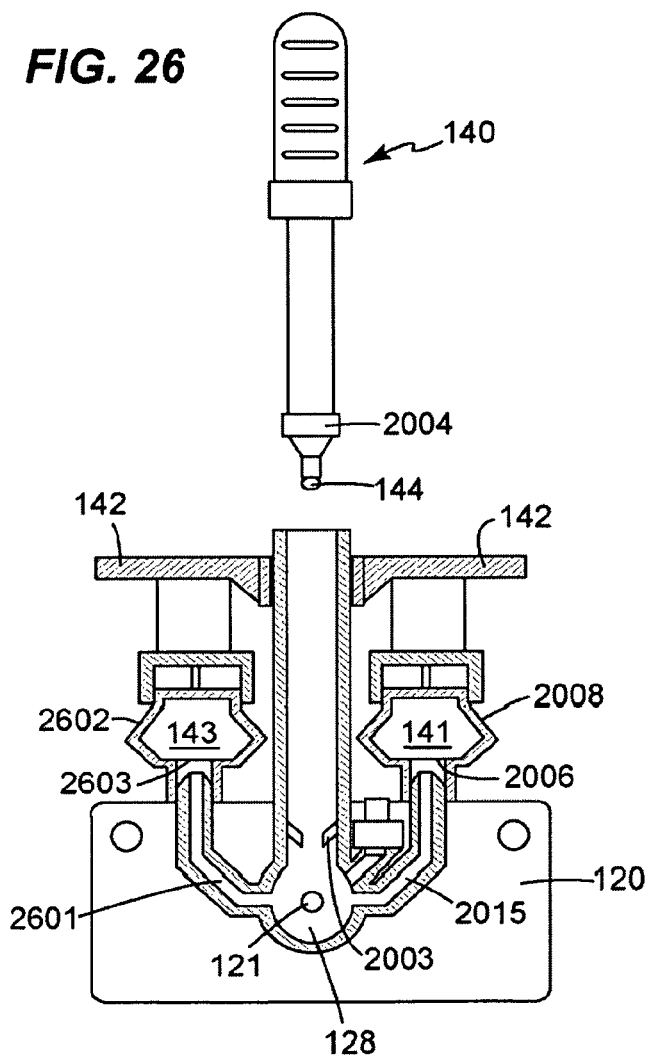
FIG. 26 is a cross-sectional view of an alternative embodiment of a collection stem and a cartridge.

FIG. 26 is a cross-sectional view of an alternative embodiment of the collection stem 140 and a cartridge 120. The collection stem 140 is elongated, but does not include a sealed vessel. Instead, a dry collector 144 is affixed to one end of the collection stem 140, and a handle is attached to the opposite end of the collector 140. A lower portion of the collection stem 140 may include a rim or gasket 2004 configured to engage a jaw 2003 formed inside a portion of the chamber 128, which is formed in the cartridge 120. A magnet 121 may be positioned proximate a lower portion of the chamber 128.

Referring to FIGS. 4, 5, 6, 7 and 26, the chamber 128 may include a pellet forming area 156 having a predetermined geometry that is configured to maximize a ratio of a pellet surface area to a pellet volume. A reservoir 2602, 2008 may be formed in the cartridge 120 and configured to contain at least one of a liquid medium and one or more reagents 143. In an embodiment, non-limiting examples of one or more reagents include one or more magnetic particles, one or more optically responsive tags, and the like. In one embodiment, the reservoir 2602 is a reagent reservoir that contains at least one reagent 143. The second reservoir 2008 may contain a liquid medium 141, which may optionally include one of one or more magnetic particles and one or more optically responsive tags.

In addition, each reservoir 2602, 2008 is selectably coupled with the chamber 120. The term "selectably coupled" means that the contents of each reservoir 2601, 2008 can be introduced into the chamber 128 upon demand by a user of the substance detection system. In one embodiment, this is accomplished by depressing an actuator 142 and rupturing a seal 2603, 2006 that respectively separates each reservoir 2601, 2008 from a channel 2603, 2015 that opens into the chamber 128. Additionally, a magnet 121 is coupled with the cartridge 120 and is moveable to the pellet forming area. The substance detection system may further include a collection stem 140 having a dry collector 144. At least the dry collector 144 is engageable with the chamber 128 of the cartridge 120, once the collection stem 140 is inserted within the cartridge 120. The dry collector 144 is configured to collect a sample of a target substance. For example, the dry collector 144 may be contacted with a sample substance 1301, which may contain at least one detection target. Thereafter, the dry collector 144 may be inserted into the chamber 128.

In one embodiment, the collection stem 140 is stored in the cartridge 120 prior to use. In another embodiment, the collection stem 140 is stored separately from the cartridge 120 prior to use. When inserted within the cartridge 120, a retaining member 2003 formed within the cartridge 120 may engage a blocking member 2004 of the collection stem 140 to prevent the collection stem 140 from being withdrawn from the cartridge 120. In one embodiment, the blocking member 2004 is an annular ring or flange that is attached to, or integrally formed in, the collection stem 140.

Illustratively, referring to FIGS. 4, 5, 6, 7, and 26, a method of operating the alternative embodiment of FIG. 26 may include collecting a sample on a dry collector 144 of a collection stem 140; inserting the collected sample and dry collection stem into the chamber 128; mixing the collected sample with the liquid medium 141, and at least one of: one or more magnetic particles, one or more optically responsive tags, and one or more reagents; and forming a pellet 180 of the one or more magnetic particles, the pellet 180 having a maximized surface area. As mentioned above, the sample may contain a detection target. The method may thereafter include interrogating the pellet 180 with a laser spectrometer to identify a substance of interest (if any) that was included in the sample collected on the dry collector 144. The pellet formation, laser interrogation, and identification of the detection target(s), if any, are performed using any of the techniques, or combinations of techniques, previously or subsequently described herein.

Figure 27:
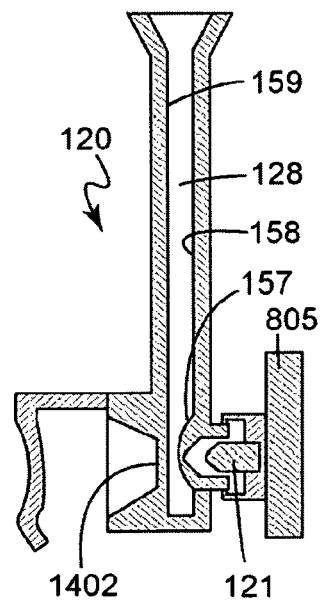
FIG. 27 is a simplified side view of an embodiment of a cartridge.

FIG. 27 is a simplified side view of an embodiment of a cartridge 120 illustrating how a magnet 121 attached to an actuator 805 may be positioned proximate a predetermined geometry 157 of a wall 158 of a chamber 128. FIG. 27 further illustrates that a sampling window 1402 may be formed in, or coupled with, an opposite wall 159 of the chamber 128.

Figure 28:
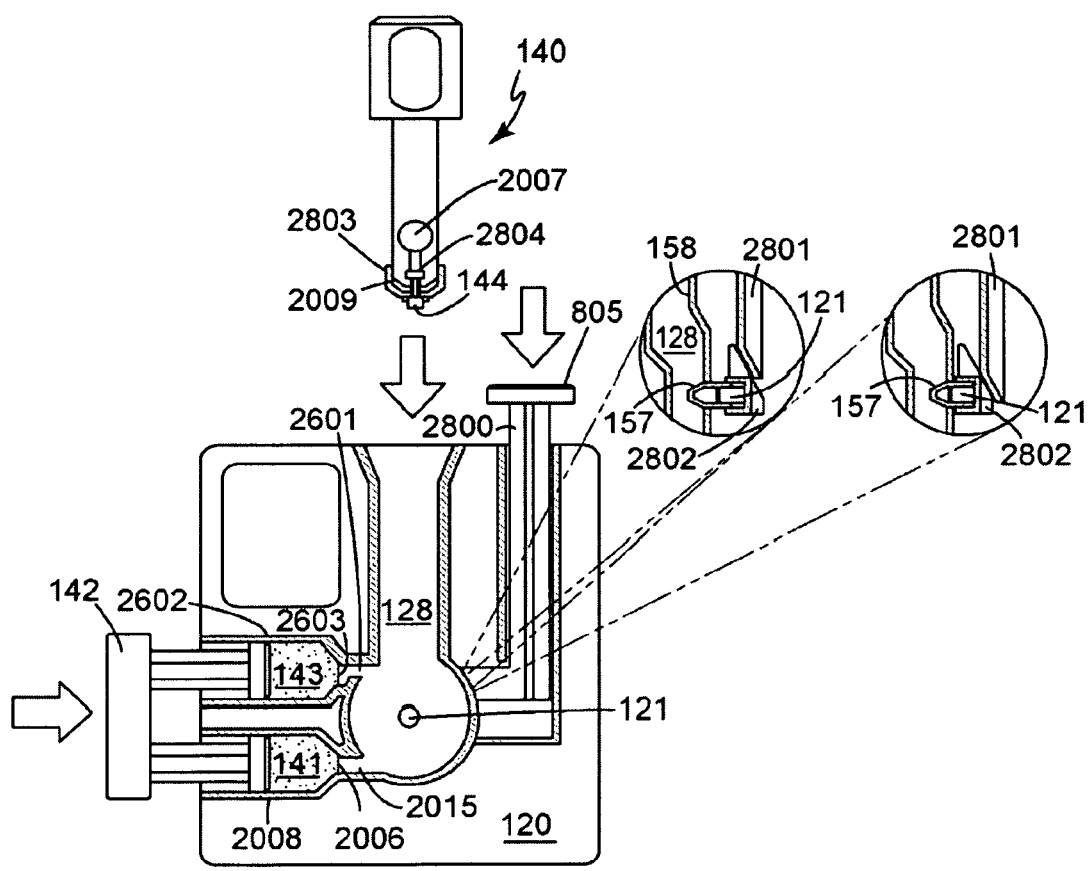
FIG. 28 is a cross-sectional view of another embodiment of a collection stem and a cartridge.

FIG. 28 is a cross-sectional view of another embodiment of a collection stem 140 and a cartridge 120. The collection stem 140 may have an elongated shape and may include a sealed vessel 2007 disposed proximate one end thereof. A handle may be attached to an opposite end of the collection stem 140. A collector 144 may be positioned in a collector housing 2803 that is slidably coupled with the one end of the collection stem 140. The collector housing 2803 may include a first channel 2009, an end of which is configured to pierce a sealed vessel seal 2804 when the collector housing 2803 is urged towards the one end of the collection stem 140.

The cartridge 120 may include a chamber 128 having a magnet 121 positioned proximate a lower portion thereof. The cartridge 120 may further include a actuator 142 coupled to both a reservoir 2602 and to a bore 2008. The reservoir 2602 may contain at least one liquid or solid reagents 143; the bore 2008 may contain a liquid medium 141. The reagent reservoir 2602 may be sealed with a reservoir seal 2603; and the bore 2008 may be sealed with a seal 2006. A reagent second channel 2601 may couple the reservoir 2602 with a lower portion of the chamber 128. A second channel 2015 may couple the bore 2008 with the lower portion of the chamber 2008. When the actuator 142 is activated, the reagents 143 and the liquid medium 141 may be concurrently expressed into the chamber 128.

The cartridge 120 may further include a magnet 121. The magnet 121 may have any shape and any geometry of pole face. Illustratively, the magnet 121 may have a generally cylindrical shape, and the magnet's pole face may comprise a tapered point. In such an embodiment, the tapered end of the magnet 121 may be configured to be positioned proximate a predetermined geometry 157 of a wall 158 of the chamber 128. A non-tapered end of the magnet 121 may be coupled with a magnet holder 2802. An angled portion of the magnet holder 2802 may be coupled with an angled tip 2801 of a shaft 2800. An actuator 805 may be coupled with an end of the shaft 2800 that is opposite the angled tip 2801. As the actuator 805 is depressed towards the housing of the cartridge 120, the angled tip 2801 exerts pressure against the angled portion of the magnet holder 2802 and thus urges the magnet 121 proximate the predetermined geometry 157. When the actuator 805 is retracted, either manually or via a biasing means such as a spring (not shown), the angled tip 2801 releases pressure from the angled portion of the magnet holder 2802, which permits the magnet 121 to move back to its original position. Although not shown, the magnet 121 and/or the magnet holder 2802 may be biased with a spring or other type of biasing means.

Figure 30:
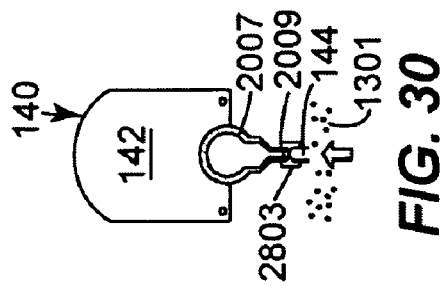
FIGS. 29 and 30 are cross-sectional views of an alternative embodiment of a collection stem.
Figure 29:
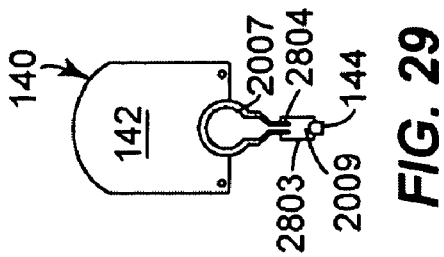

FIGS. 29 and 30 are cross-sectional views of another embodiment of a collection stem 140. The collection stem 140 may include a actuator 142 having a sealed vessel 2007 coupled with an end thereof. The sealed vessel 2007 may be sealed with a sealed vessel seal 2804 and may contain a first quantity of liquid medium. A collection stem housing 2803 may be slidably coupled with an end of the sealed vessel 2007. The collection stem housing 2803 may include a tapered first channel 2009. The first channel 2009 may be coupled with a collector 144 affixed to the collector housing 2803. An end of the first channel 2009 may be configured to pierce the sealed vessel seal 2804 when the collector housing 2803 is urged toward the end of the sealed vessel 2007, as shown in FIG. 33. In this manner, the collector 144 may be wetted with the liquid medium from the sealed vessel 2007 to improve collection of a sample substance 1301.

Figure 31:
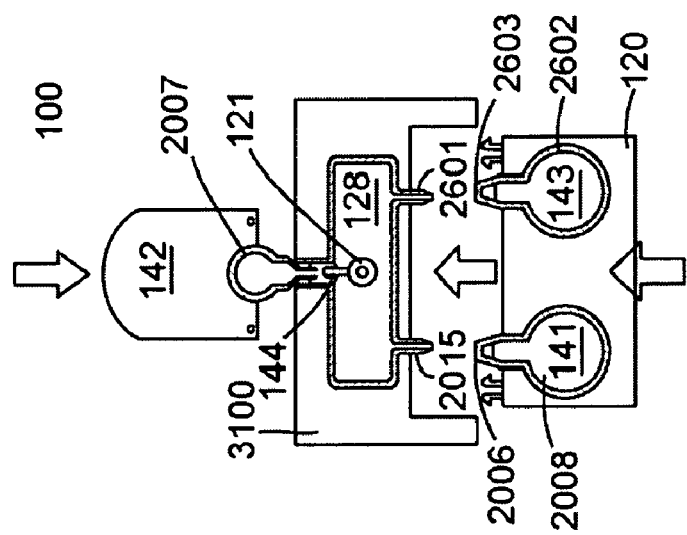
FIG. 31 is a cross-sectional view of another embodiment of a portable substance identification system.

FIG. 31 is a cross-sectional view of another embodiment of a portable substance identification system 100. The system 100 may include a collection stem 140 as shown in and described with respect to FIGS. 29 and 30. The system 100 may further include a substance identification device 101 having a chamber 128 formed therein. A magnet 121 may be positioned proximate a pellet forming area of the chamber 128. Additionally, the chamber 128 may include a second channel 2015 and a channel 2601. A free end of the second channel 2015 may be configured to pierce a reservoir seal 2006 of a reservoir 2006 formed in a cartridge 120. A free end of the reagent channel 2601 may be configured to pierce a seal 2603 of a reservoir 2602 formed in the cartridge 120.

Figure 32:
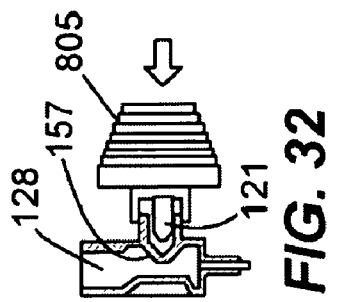
FIG. 32 is a cross-sectional view of an embodiment of a chamber illustrating a magnet coupled with an actuator.

FIG. 32 is a cross sectional view of an embodiment of a chamber 128 illustrating a magnet 121 coupled with an actuator 805. In use, force applied to the actuator 805 moves the magnet 121 towards or away from a predetermined geometry 157 of a wall 158 of the chamber 128, as previously described.

Viewed together, FIGS. 29, 30, 31, and 32 illustrate an embodiment of a method of identifying at least one detection target. As shown in FIGS. 29 and 30, a collector 140 is removed from its packaging, and pressure is applied to urge the collector housing 2803 towards the end of the sealed vessel 2007. This causes the first channel 2009 to rupture the sealed vessel seal. Liquid medium from the sealed vessel 2007 then flows through the first channel 2009 and wets the collector 144. The collector 144 may then be contacted with a sample substance 1301, which may contain at least one detection target.

The collector 144 may then be inserted within a portion of the chamber 128. The cartridge 120 may then be coupled with a housing 3100 of the chamber 128 to mate the second channel 2015 with the bore 2008 and to mate the channel 2601 with the reservoir 2602. As these matings occur, a free end of the second channel 2015 ruptures a reservoir seal 2006, allowing liquid medium 141 to flow through the second channel 2015 and into the chamber 128. As these matings occur, a free end of the channel 2601 ruptures a seal 2603, allowing reagents 143 to flow through the channel 2601 and into the chamber 128.

Thereafter, the chamber 128 may be gently agitated to mix any detection targets with the liquid medium 141 and the reagents 143. After a predetermined time, the actuator 805 may be activated to urge the magnet 121 towards the wall 158 of the chamber 128. When an end of the magnet 121 is suitably positioned, a magnetic field or magnetic field gradient exerted by the end of the magnet 121 causes a pellet (not shown) to form on a surface of the predetermined geometry 157, which may be configured to maximize a surface area of the pellet. Thereafter, a laser emitted by a laser source, which may form part of a Raman spectrometer, may be used to scan the pellet to identify the detection target(s) (if any) collected by the collector 144.

Following analysis using Raman spectroscopic techniques, the cartridge 120, the chamber 128, and the collection stem 140 may be decontaminated and/or disposed without disassembly. Additionally, a validation of the results of the Raman spectroscopic analysis may be performed as described above.

In an embodiment, the cartridge 120 may include a disposable part, and a non-disposable part. The disposable part of the cartridge 120 may include at least the collector 144.

Referring again to FIG. 1, in addition to the description provided above, an embodiment of the portable substance identification device 101 can be configured to receive data about the cartridge 120 and/or to transmit data from the memory 104 and/or to transmit a validation, or other processed data, output by the processor 103 to the cartridge 120. The received data about the cartridge 120 can include, but is not limited to, a unique manufacturer identifier, an expiration date, a predetermined agitation cycle, a type of assay to be performed, and the like. The memory 104 can store the received data about the cartridge 120, processed data output by the processor 103, and/or other data, such as one or more pre-loaded unique manufacturer identifiers.

The processor 103 can be configured to determine whether some or all of the received data about the cartridge 120 is valid or invalid. For example, in one embodiment, the processor 103 is configured to determine whether a unique manufacturer identifier received from the cartridge 120 is valid or invalid. A valid manufacturer identifier can indicate the cartridge 120 was produced by an authorized source. An invalid manufacturer identifier can indicate the cartridge 120 was produced by an unauthorized source. In one embodiment, the processor 103 is configured to determine whether an expiration date received from the cartridge 120 is valid or has lapsed. The determination of the processor 103 can be stored in the memory 104 of the portable substance identification device 101.

Referring again to FIGS. 1 and 17, an embodiment of the agitator 160 may be portable and may contain a power source 165, such as one or more batteries. The agitator 160 may further include a processor 162, or microcontroller, coupled with a memory 163. The agitator 160 may further include a communicator, such as a radio frequency identification tag reader or a wireless transceiver, configured to receive data from and/or transmit data to the cartridge 120. The memory 163 of the agitator 160 may be configured to store data such as a pre-loaded unique manufacturer identifier, processed data output by the processor 162 of the agitator 160, and/or received data about the cartridge 120.

The processor 162 of the agitator 160 can be configured to determine whether some or all of the data received from the cartridge 120 is valid or invalid. For example, in one embodiment, the processor 162 of the agitator 160 is configured to determine whether a unique manufacturer identifier received from the cartridge 120 is valid or invalid. In one embodiment, the processor 162 of the agitator 160 is configured to determine whether an expiration date received from the cartridge 120 is valid or has lapsed. In one embodiment, the processor 162 of the agitator 160 is configured to determine a predetermined agitation cycle from the received data about the cartridge 120. The determination of the processor 162 of the agitator 160 can be stored in the memory 163 of the agitator 160.

Although specific features of various embodiments of the invention may be shown in some drawings and not in others, this is for convenience only. In accordance with the principles of the invention, the feature(s) of one drawing may be combined with any or all of the features in any of the other drawings. The words "including", "comprising", "having", and "with" as used herein are to be interpreted broadly and comprehensively and are not limited to any physical interconnection. Moreover, any embodiments disclosed herein are not to be interpreted as the only possible embodiments. Rather, modifications and other embodiments are intended to be included within the scope of the appended claims.

What is claimed is:

1. A portable substance identification system, comprising:
   a cartridge having a chamber, wherein the chamber includes a pellet forming area on an inner surface of an exterior wall of the chamber, the pellet forming area having a predetermined geometry that is configured to maximize a ratio of a pellet surface area to a pellet volume;
   a magnet configured to form a pellet in the pellet forming area;
   a collection stem having a dry collector, wherein at least the dry collector is engageable with the chamber of the cartridge, and is configured to collect a sample; and
   a spectrometer and a laser source, wherein the cartridge is configured to couple with the portable substance identification device, the laser source configured to illuminate the pellet in the pellet forming area.

2. The portable substance identification system of claim 1, further comprising:
   a reservoir formed in the cartridge and configured to contain at least one of a liquid medium and one or more reagents, wherein the reservoir is selectably coupled with the chamber.

3. The portable substance identification system of claim 2, further comprising:
   an actuator coupled with the reservoir and configured to be moved relative to the reservoir;
   a channel coupling the reservoir with the chamber; and
   a seal disposed at an end of the reservoir, wherein the seal is configured to rupture when the actuator is moved relative to the reservoir.

4. The portable substance identification system of claim 2, wherein the liquid medium is a buffer solution.

5. The portable substance identification system of claim 1, wherein the laser source is positioned on a same side of the chamber as the magnet.

6. The portable substance identification system of claim 1, wherein the cartridge includes data about the cartridge, the data about the cartridge including a unique manufacturer identifier.

7. The portable substance identification system of claim 6, wherein the data about the cartridge further includes at least one of an expiration date, a type of assay, and a predetermined agitation cycle.

8. The portable substance identification system of claim 6, wherein the portable substance identification device includes a processor coupled with a memory, the processor configured to receive and process the data about the cartridge.

9. The portable substance identification system of claim 8, wherein the processor is further configured to determine whether the unique manufacturer identifier received from the cartridge is valid or invalid.

10. The portable substance identification system of claim 1, wherein the spectrometer is a Raman spectrometer configured to scan the pellet to identify a detection target, if any, collected by the dry collector.

11. A method, comprising:
    collecting a sample on a dry collector of a collection stem;
    inserting the collected sample and dry collector into a chamber of a cartridge that is configured to couple with a portable substance identification device;
    mixing the collected sample with the liquid medium and one or more magnetic particles;
    forming a pellet of the one or more magnetic particles in a pellet forming area in the chamber, the pellet having a maximized surface area; and
    emitting a laser at the pellet in the pellet forming area.

12. The method of claim 11, further comprising:
    analyzing the pellet with a Raman spectrometer to identify a detection target, if any, included in the sample collected on the dry collector.

13. The method of claim 12, further comprising:
    outputting an identification of the detection target.

* * * * *